US006818424B2

(12) United States Patent
DiCosimo et al.

(10) Patent No.: US 6,818,424 B2
(45) Date of Patent: Nov. 16, 2004

(54) PRODUCTION OF CYCLIC TERPENOIDS

(75) Inventors: Deana J. DiCosimo, Rockland, DE (US); Mattheos Koffas, Wilmington, DE (US); James M. Odom, Kennett Square, PA (US); Siqun Wang, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 447 days.

(21) Appl. No.: 09/938,956

(22) Filed: Aug. 24, 2001

(65) Prior Publication Data

US 2002/0142408 A1 Oct. 3, 2002

Related U.S. Application Data

(60) Provisional application No. 60/229,907, filed on Sep. 1, 2000, and provisional application No. 60/229,858, filed on Sep. 1, 2000.

(51) Int. Cl.$^7$ ................................................ C12P 5/00
(52) U.S. Cl. ................................. 435/166; 435/252.3
(58) Field of Search .............................. 435/166, 252.3

(56) References Cited

U.S. PATENT DOCUMENTS

| | | | |
|---|---|---|---|
| 4,348,476 A | 9/1982 | Hou | 435/123 |
| 5,750,821 A | 5/1998 | Inomata et al. | 585/943 |

FOREIGN PATENT DOCUMENTS

| | | |
|---|---|---|
| WO | WO 9511913 A1 | 5/1995 |
| WO | WO 9633821 A1 | 10/1996 |
| WO | WO 9902030 A1 | 1/1999 |
| WO | WO 2000007718 A1 | 2/2000 |
| WO | WO 0022150 A3 | 4/2000 |

OTHER PUBLICATIONS

Colby et al., 4S–Limonene synthase from the Oil Glands of Spearmint (Mentha Spicata), Journal of Biological Chemistry. American Society of Biological Chemists, vol. 266, No. 31, Nov. 5, 1993, pp. 23016–23024, XP000939217.
Bohlmann et al., Monoterpene Synthases from Grand Fir (Abies Grandis)CDNA Isolation, Characterization, and functional Expression of Myrcene Synthase, (–)–(4S)–Limonene Synthase, and (–)–(iS,5S)–Pinene Synthase, Journal of Biological Chemistry, American Society of Biological Chemists, vol. 272, No. 35, Aug. 29, 1997, XP000938120.
Yuba et al., Arch Biochem Biophys 332:280–287, 1996.
Sharpe, D. H., BioProtein Manfacture 1989. Ellis Horwood series in applied science and industrial technology New York: Halstead Press.
Villadsen, John. Recent Trends Chem. React. Eng., Proc. Int. Chem. React. Eng. Conf., $2^{nd}$, 1987, vol. 2, 320–333. Editors Kulkami et al., Publisher: Wiley East, New Delhi, India.
Naguib. M., Proc. OAPEC Symp. Petroprotein, Pap. 1980, Meeting Date 1979, 253–277, Publisher Organ. Arab Pet. Exporting Countries, Kuwait, Kuwait.
Tsien et al., Gas, Oil, Coal, Environ. Biotechnol 2, Pap. Int. IGT Symp. Gas, Oil, Coal. Environ. Biotechnol., 2nd, 1990, 83–104. Editors Akin et al., Publisher Inst Gas Technol. Chicago, IL.
Merkley et al., Biorem, Recalcitrant Org., Pap Int. In Situ On–Site Bioreclam. Symp., $3^{rd}$, 1995, 165–74. Editors Hinches et al., Publisher: Batelle Press, Columbus, OH.
Meyer et al., Microb. Releases, 1993, 2(1), pp. 11–22.
Murrell et al., Arch. Microbiol., 2000, 173(5–6), 325–332.
Gngoryan, E. A., Kinet. Catal., 1999, 40(3), 350–363.
Lois et al., Proc. Natl. Acad. Sci. USA 95: 2105–2110, 1998.
Takahashi et al., Proc. Natl. Acad. Sci. USA 95: 9879–9884, 1998.
Swiss Prot#Q46893.
Rohdich et al., Proc. Natl. Acad. Sci. USA 96:11758–11763, 1990.
SwissProt #P24209.
Luttgen et al., Proc. Natl. Acad. Sci. USA, 97: 1062–1067, 2000.
Herz, Proc. Natl. Acad. Sci. USA 97: 2486–2490, 2000.
Swiss Prot #P36663.
Weng et al., J. Biol. Chem., 261: pp. 5568–5574, 1986.
Lange and Croteau, Proc. Natl. Acad. Sci. USA 96: 13714–13719, 1999.
Cunningham et al., J. Bac. 182 No. 20: 5841–5848, 2000.
Ohto et al., Plant Mol. Biol. 40(2), 307–321, 1999.
Beschastnyi et al., Inst. Biochem. Physiol. Microor., Pushchino, Russia, Bickhimiya (Moscow) 1992, 57(8), pp. 1215–1221.
Shishkina et al., Inst. Bikhim. Fiziol. Mikrorg., Pushchino, Russia, Mikrobiologlys, 1990, 59(4), 533–8.
Trotsenko et al., Studies on Phosphate metabolism in obligate mehtanotrophs, Ferris Microbiology Reviews 87, 1990, pp. 267–272.

Primary Examiner—Nashaat T. Nashed

(57) ABSTRACT

A methanotrophic bacterium has been genetically engineered to produce cyclic terpenoids from geranyl pyrophosphate.

7 Claims, 8 Drawing Sheets

SEQUENCE LISTING

<160> NUMBER OF SEQ ID NOS: 7

<210> SEQ ID NO 1
<211> LENGTH: 26
<212> TYPE: DNA
<213> ORGANISM: Primer

<400> SEQUENCE: 1
atgagacgat ccggaaacta caaccc                26

<210> SEQ ID NO 2
<211> LENGTH: 29
<212> TYPE: DNA
<213> ORGANISM: Primer

<400> SEQUENCE: 2
tcatgcaaag ggctcgaata aggttctgg              29

<210> SEQ ID NO 3
<211> LENGTH: 22
<212> TYPE: DNA
<213> ORGANISM: Primer

<400> SEQUENCE: 3
atgattgaac aagatggatt gc                    22

<210> SEQ ID NO 4
<211> LENGTH: 21
<212> TYPE: DNA
<213> ORGANISM: Primer

<400> SEQUENCE: 4
aagctttcaa aagaactcgt c                                             21

<210> SEQ ID NO 5
<211> LENGTH: 11575
<212> TYPE: DNA
<213> ORGANISM: Plasmid

<400> SEQUENCE: 5

```
tcccgtggcg tcgaaagtgc ggcaccatag gtatcagtca ccgcgatgag atcccttacc    60
attccagagt ctggcggttg attattaatt tgctgatata gagcctcagc ccgctggcga   120
aattcattac gtaaatcaaa ggcttcaggt cggggtaatt taaaactaag ctgaatgatt   180
ttctggagat agcggctgcc atcttcgata ttcagcgcat gttcaacggc atgagtgata   240
atctgcctgt cataacagag aatatgggta agcggggca gatcggctac tgcacgcaca   300
agcctgaaca cttccgccac ctgggatggc tccagtcggt ccagatcatc catgacaaca   360
atgaacttca gatccagact caccagttgt cctgcaattt cagcccgaag cttgcgtgta   420
ttcgtactcg gctggtttga aacccgtgcg cgcgtcaagg atgatcccgg catcttgccc   480
ttcttctttc cgttactggc ggccttcggc ggcatgatgt tgctggcaca ctcccatgtc   540
ggcttcgaag ccaaaaccgc gttcttgatc caggtcggcc ataccttgat gggcgtattc   600
tcgctgatcc tggcctgcgg tcgctggctg gaactcaagc tcgattctcc cggcaaaaat   660
attgccggtt ttatttcagt gttcgccttg tttcaaatcg gcgtcatcct gatgttctac   720
cgtgaaccct tgtactgatt atgaaactga ccaccgacta tcccttgctt aaaaacatcc   780
acacgccggc ggacatacgc gcgctgtcca aggaccagct ccagcaactg gctgacgagg   840
tgcgcggcta tctgacccac acggtcagca tttccggcgg ccattttgcg gccggcctcg   900
gcaccgtgga actgaccgtg gccttgcatt atgtgttcaa tacccccgtc gatcagttgg   960
tctgggacgt gggccatcag gcctatccgc acaagattct gaccggtcgc aaggagcgca  1020
tgccgaccat tcgcaccctg gcggggtgt cagcctttcc ggcgcgggac gagagcgaat  1080
acgatgcctt cggcgtcggc cattccagca cctcgatcag cgcggcactg gcatggccat  1140
tgcgtcgca gctgcgcggc aagacaaga agatggtagc catcatcggc gacggttcca  1200
tcaccggcgg catggcctat gaggcgatga atcatgccgg cgatgtgaat gccaacctgc  1260
tggtgatctt gaacgacaac gatatgtcga tctcgccgcc ggtcggggcg atgaacaatt  1320
atctgaccaa ggtgttgtcg agcaagtttt attcgtcggt gcgggaagag agcaagaaag  1380
ctctggccaa gatgccgtcg gtgtgggaac tggcgcgcaa gaccgaggaa cacgtgaagg  1440
gcatgatcgt gccggtacc ttgttcgagg aattgggctt caattatttc ggcccgatcg  1500
acggccatga tgtcgagatg ctggtgtcga ccctggaaaa tctgaaggat ttgaccgggc  1560
cggtattcct gcatgtggtg accaagaagg gcaaaggcta tgcgccagcc gagaaagacc  1620
cgttggccta ccatggcgtg ccggctttcg atccgaccaa ggatttcctg cccaaggcgg  1680
cgccgtcgcc gcatccgacc tataccgagg tgttcggccg ctggctgtgc gacatggcgg  1740
ctcaagacga gcgcttgctg ggcatcacgc cggcgatgcg cgaaggctct ggtttggtgg  1800
```

-continued

```
aattctcaca gaaatttccg aatcgctatt tcgatgtcgc catcgccgag cagcatgcgg    1860
tgaccttggc cgccggccag gcctgccagg gcgccaagcc ggtggtggcg atttattcca    1920
ccttcctgca acgcggttac gatcagttga tccacgacgt ggccttgcag aacttagata    1980
tgctctttgc actggatcgt gccggcttgg tcggcccgga tggaccgacc catgctggcg    2040
cctttgatta cagctacatg cgctgtattc cgaacatgct gatcatggct ccagccgacg    2100
agaacgagtg caggcagatg ctgaccaccg gcttccaaca ccatgcccg gcttcggtgc      2160 gctatccgcg cggcaaaggg cccggggcgg caatcgatcc gaccctgacc gcgctggaga    2220
tcggcaaggc cgaagtcaga caccacggca gccgcatcgc cattctggcc tggggcagca    2280
tggtcacgcc tgccgtcgaa gccggcaagc agctgggcgc gacggtggtg aacatgcgtt    2340
tcgtcaagcc gttcgatcaa gccttggtgc tggaattggc caggacgcac gatgtgttcg    2400
tcaccgtcga ggaaaacgtc atcgccggcg gcgctggcag tgcgatcaac accttcctgc    2460
aggcgcagaa ggtgctgatg ccggtctgca acatcggcct gcccgaccgc ttcgtcgagc    2520
aaggtagtcg cgaggaattg ctcagcctgg tcggcctcga cagcaagggc atcctcgcca    2580
ccatcgaaca gttttgcgct taaacttgcc gatgctggaa atcattcaac tgccagtcct    2640
gaacgacaac tcgaggacat cagtgcttat ttcgtcggca aaaatgggg caaggacaaa      2700 ctcgcgcctg aaatcagccc tggcaaaacc gtgcaaggca tgtatggtgc attggcttca    2760
gcgatgattt gcgcgatagg tttgcgcgtt tattacggct tttcggcctt ggaatcggat    2820
ggcgcggaat tggcggtcct gatgtcgata gatttgctga ttttgtcggt gttgaccgtg    2880
ctggtatcca tttacggcga tttgtttttc agtctggtca agcgaatcaa aggcgtcaag    2940
gatagtggca ccttgttgcc gggtcatggc ggtatcctcg ataggtgga cagcatcatt     3000 gcggcggcac cgttttttcta tgccggtatc gtgctgatcg gacggagcgt attcgaatga    3060
aaggtatttg catattgggc gctaccggtt cgatcggtgt cagcacgctg gatgtcgttg    3120
ccaggcatcc ggataaatat caagtcgttg cgctgaccgc caacggcaat atcgacgcat    3180
tgtatgaaca atgcctggcc caccatccgg agtatgcggt ggtggtcatg gaaagcaagg    3240
tagcagagtt caaacagcgc attgccgctt cgccggtagc ggatatcaag gtcttgtcgg    3300
gtagcgaggc cttgcaacag gtggccacgc tggaaaacgt cgatacggtg atggcggcta    3360
tcgtcggcgc ggccggattg ttgccgacct tggccgcggc caaggccggc aaaaccgtgc    3420
tgttggccaa caaggaagcc ttggtgatgt cgggacaaat cttcatgcag gccgtcagcg    3480
attccggcgc tgtgttgctg ccgatagaca gcgagcacaa cgccatcttt cagtgcatgc    3540
cggcgggtta tacgccaggc catacagcca acaggcgcg ccgcatttta ttgaccgctt      3600
ccggtggccc atttcgacgg acgccgatag aaacgttgtc cagcgtcacg ccggatcagg    3660
ccgttgccca tcctaaatgg gacatggggc gcaagatttc ggtcgattcc gccaccatga    3720
tgaacaaagg tctcgaactg atcgaagcct gcttgttgtt caacatggag cccgaccaga    3780
ttgaagtcgt cattcatccg cagagcatca ttcattcgat ggtggactat gtcgatggtt    3840
cggttttggc gcagatgggt aatcccgaca tgcgcacgcc gatagcgcac gcgatggcct    3900
ggccggaacg ctttgactct ggtgtggcgc cgctggatat tttcgaagta gggcacatgg    3960
atttcgaaaa acccgacttg aaacggtttc cttgtctgag attggcttat gaagccatca    4020
agtctggtgg aattatgcca acggtattga acgcagccaa tgaaattgct gtcgaagcgt    4080
ttttaaatga agaagtcaaa ttcactgaca tcgcggtcat catcgagcgc agcatggccc    4140
agtttaaacc ggacgatgcc ggcagcctcg aattggtttt gcaggccgat caagatgcgc    4200
```

```
gcgaggtggc tagagacatc atcaagacct tggtagctta atggaaaccc ttcacaccct      4260
gttttattcc atcgttgcga tcgcgattct ggttgcctct agatcggatc cgtcgacact      4320
gcagagcttg cagtgggctt acatggcgat agctagactg ggcggtttta tggacagcaa      4380
gcgaaccgga attgccagct ggggcgccct ctggtaaggt tgggaagccc tgcaaagtaa      4440
actggatggc tttcttgccg ccaaggatct gatggcgcag gggatcaaga tctgatcaag      4500
agacaggatg aggatcgttt cgcatgattg aacaagatgg attgcacgca ggttctccgg      4560
ccgcttgggt ggagaggcta ttcggctatg actgggcaca acagacaatc ggctgctctg      4620
atgccgccgt gttccggctg tcagcgcagg ggcgcccggt tcttttttgtc aagaccgacc      4680 tgtccggtgc cctgaatgaa ctgcaggacg aggcagcgcg gctatcgtgg ctggccacga      4740
cgggcgttcc ttgcgcagct gtgctcgacg ttgtcactga agcgggaagg gactggctgc      4800
tattgggcga agtgccgggg caggatctcc tgtcatctca ccttgctcct gccgagaaag      4860
tatccatcat ggctgatgca atgcggcggc tgcatacgct tgatccggct acctgcccat      4920
tcgaccacca agcgaaacat cgcatcgagc gagcacgtac tcggatggaa gccggtcttg      4980
tcgatcagga tgatctggac gaagagcatc aggggctcgc gccagccgaa ctgttcgcca      5040
ggctcaaggc gcgcatgccc gacggcgagg atctcgtcgt gacccatggc gatgcctgct      5100
tgccgaatat catggtggaa aatggccgct tttctggatt catcgactgt ggccggctgg      5160
gtgtggcgga ccgctatcag gacatagcgt tggctacccg tgatattgct gaagagcttg      5220
gcggcgaatg ggctgaccgc ttcctcgtgc tttacggtat cgccgctccc gattcgcagc      5280
gcatcgcctt ctatcgcctt cttgacgagt tcttctgaaa gcttggctgc cattttttggg      5340 gtgaggccgt tcgcggccga ggggcgcagc ccctgggggg atgggaggcc cgcgttagcg      5400
ggccgggagg gttcgagaag ggggggcacc cccttcggc gtgcgcggtc acgcgcacag      5460
ggcgcagccc tggttaaaaa caaggtttat aaatattggt ttaaaagcag gttaaaagac      5520
aggttagcgg tggccgaaaa acggggcgga aacccttgca aatgctggat tttctgcctg      5580
tggacagccc ctcaaatgtc aataggtgcg cccctcatct gtcagcactc tgcccctcaa      5640
gtgtcaagga tcgcgcccct catctgtcag tagtcgcgcc cctcaagtgt caataccgca      5700
gggcacttat ccccaggctt gtccacatca tctgtgggaa actcgcgtaa atcaggcgt      5760 tttcgccgat ttgcgaggct ggccagctcc acgtcgccgg ccgaaatcga gcctgcccct      5820
catctgtcaa cgccgcgccg ggtgagtcgg cccctcaagt gtcaacgtcc gcccctcatc      5880
tgtcagtgag ggccaagttt ccgcgaggt atccacaacg ccggcggccg cggtgtctcg      5940
cacacggctt cgacgcgtt tctggcgcgt ttgcagggcc atagacgcc gccagcccag      6000 cggcgagggc aaccagcccg gtgagcgtcg gaaagggtcg acggatcttt ccgctgcat      6060 aaccctgctt cggggtcatt atagcgattt tttcggtata tccatccttt ttcgcacgat      6120
atacaggatt ttgccaaagg gttcgtgtag actttccttg gtgtatccaa cggcgtcagc      6180
cgggcaggat aggtgaagta ggcccacccg cgagcgggtg ttccttcttc actgtccctt      6240
attcgcacct ggcggtgctc aacgggaatc ctgctctgcg aggctggccg gctaccgccg      6300
gcgtaacaga tgagggcaag cggatggctg atgaaaccaa gccaaccagg aagggcagcc      6360
cacctatcaa ggtgtactgc cttccagacg aacgaagagc gattgaggaa aaggcggcgg      6420
cggccggcat gagcctgtcg gcctacctgc tggccgtcgg ccaggctac aaaatcacgg      6480 gcgtcgtgga ctatgagcac gtccgcgagc tggcccgcat caatgcgac ctgggccgcc      6540
```

```
tgggcggcct gctgaaactc tggctcaccg acgacccgcg cacgcgcgg ttcggtgatg    6600 ccacgatcct cgccctgctg gcgaagatcg aagagaagca ggacgagctt ggcaaggtca    6660
tgatgggcgt ggtccgcccg agggcagagc catgactttt ttagccgcta aaacggccgg    6720
ggggtgcgcg tgattgccaa gcacgtcccc atgcgctcca tcaagaagag cgacttcgcg    6780
gagctggtat tcgtgcaggg caagattcgg aataccaagt acgagaagga cggccagacg    6840
gtctacggga ccgacttcat tgccgataag gtggattatc tggacaccaa ggcaccaggc    6900
gggtcaaatc aggaataagg gcacattgcc ccggcgtgag tcgggcaat cccgcaagga     6960 gggtgaatga atcggacgtt tgaccggaag gcatacaggc aagaactgat cgacgcgggg    7020
ttttccgccg aggatgccga aaccatcgca agccgcaccg tcatgcgtgc gccccgcgaa    7080
accttccagt ccgtcggctc gatggtccag caagctacgg ccaagatcga gcgcgacagc    7140
gtgcaactgg ctcccctgc cctgcccgcg ccatcggccg ccgtggagcg ttcgcgtcgt     7200
ctcgaacagg aggcggcagg tttggcgaag tcgatgacca tcgacacgcg aggaactatg    7260
acgaccaaga agcgaaaaac cgccggcgag gacctggcaa acaggtcag cgaggccaag     7320 caggccgcgt tgctgaaaca cacgaagcag cagatcaagg aaatgcagct ttccttgttc    7380
gatattgcgc cgtggccgga cacgatgcga gcgatgccaa acgacacggc ccgctctgcc    7440
ctgttcacca cgcgcaacaa gaaaatcccg cgcgaggcgc tgcaaaacaa ggtcattttc    7500
cacgtcaaca aggacgtgaa gatcacctac accggcgtcg agctgcgggc cgacgatgac    7560
gaactggtgt ggcagcaggt gttggagtac gcgaagcgca cccctatcgg cgagccgatc    7620
accttcacgt tctacgagct ttgccaggac ctgggctggt cgatcaatgg ccggtattac    7680
acgaaggccg aggaatgcct gtcgcgccta caggcgacgg cgatgggctt cacgtccgac    7740
cgcgttgggc acctggaatc ggtgtcgctg ctgcaccgct tccgcgtcct ggaccgtggc    7800
aagaaaacgt cccgttgcca ggtcctgatc gacgaggaaa tcgtcgtgct gtttgctggc    7860
gaccactaca cgaaattcat atgggagaag taccgcaagc tgtcgccgac ggcccgacgg    7920
atgttcgact atttcagctc gcaccgggag ccgtacccgc tcaagctgga accttccgc     7980 ctcatgtgcg gatcggattc caccgcgtg aagaagtggc gcgagcaggt cggcgaagcc     8040
tgcgaagagt tgcgaggcag cggcctggtg gaacacgcct gggtcaatga tgacctggtg    8100
cattgcaaac gctagggcct tgtggggtca gttccggctg ggggttcagc agccagcgct    8160
ttactggcat ttcaggaaca agcgggcact gctcgacgca cttgcttcgc tcagtatcgc    8220
tcgggacgca cggcgcgctc tacgaactgc cgataaacag aggattaaaa ttgacaattg    8280
tgattaaggc tcagattcga cggcttggag cggccgacgt gcaggatttc gcgagatcc    8340 gattgtcggc cctgaagaaa gctccagaga tgttcgggtc cgtttacgag cacgaggaga    8400
aaaagcccat ggaggcgttc gctgaacggt tgcgagatgc cgtggcattc ggcgcctaca    8460
tcgacggcga gatcattggg ctgtcggtct tcaaacagga ggacgcccc aaggacgctc     8520 acaaggcgca tctgtccggc gttttcgtgg agcccgaaca gcgaggccga ggggtcgccg    8580
gtatgctgct gcggcgttg ccggcgggtt tattgctcgt gatgatcgtc cgacagattc     8640
caacgggaat ctggtggatg cgcatcttca tcctcggcgc acttaatatt tcgctattct    8700
ggagcttgtt gtttatttcg gtctaccgcc tgccgggcgg ggtcgcggcg acggtaggcg    8760
ctgtgcagcc gctgatggtc gtgttcatct ctgccgctct gctaggtagc ccgatacgat    8820
tgatggcggt cctgggggct atttgcgaa ctgcgggcgt ggcgctgttg gtgttgacac      8880
caaacgcagc gctagatcct gtcggcgtcg cagcgggcct ggcgggggcg gtttccatgg    8940
```

-continued

```
cgttcggaac cgtgctgacc cgcaagtggc aacctcccgt gcctctgctc acctttaccg    9000
cctggcaact ggcggccgga ggacttctgc tcgttccagt agctttagtg tttgatccgc    9060
caatcccgat gcctacagga accaatgttc tcggcctggc gtggctcggc ctgatcggag    9120
cgggtttaac ctacttcctt tggttccggg ggatctcgcg actcgaacct acagttgttt    9180
ccttactggg ctttctcagc ccggggaccg ccgtgttgct aggatggttg ttcttggatc    9240
agacgctgag tgcgcttcaa atcatcggcg tcctgctcgt gatcgggagt atctggctgg    9300
gccaacgttc caaccgcact cctagggcgc gtatagcttg ccggaagtcg ccttgacccg    9360
catggcatag gcctatcgtt tccacgatca gcgatcggct cgttgccctg cgccgctcca    9420
aagcccgcga cgcagcgccg gcaggcagag caagtagagg gcagcgcctg caatccatgc    9480
ccacccgttc cacgttgtta tagaagccgc atagatcgcc gtgaagagga ggggtccgac    9540
gatcgaggtc aggctggtga gcgccgccag tgagccttgc agctgcccct gacgttcctc    9600
atccacctgc ctggacaaca ttgcttgcag cgccggcatt ccgatgccac ccgaagcaag    9660
caggaccatg atcgggaacg ccatccatcc ccgtgtcgcg aaggcaagca ggatgtagcc    9720
tgtgccgtcg gcaatcattc cgagcatgag tgcccgcctt tcgccgagcc gggcggctac    9780
agggccggtg atcattgcct gggcgagtga atgcagaatg ccaaatgcgg caagcgaaat    9840
gccgatcgtg gtcgcgtccc agtgaaagcg atcctcgccg aaaatgaccc aaagcgcggc    9900
cggcaccctgt ccgacaagtt gcatgatgaa gaagaccgcc atcagggcgg cgacgacggt    9960
catgcccgg gcccaccgga acgaagcgag cgggttgaga gcctcccggc gtaacggccg    10020
gcgttcgcct ttgtgcgact ccggcaaaag gaaacagccc gtcaggaaat tgaggccgtt    10080
caaggctgcc gcggcgaaga acggagcgtg gggggagaaa ccgcccatca gcccaccgag    10140
cacaggtccc gcgaccatcc cgaacccgaa acaggcgctc atgaagccga agtgccgcgc    10200
gcgctcatcg ccatcagtga tatcggcaat ataagcgccg gctaccgccc cagtcgcccc    10260
ggtgatgccg gccacgatcc gtccgatata gagaacccaa aggaaaggcg ctgtcgccat    10320
gatggcgtag tcgacagtgg cgccggccag cgagacgagc aagattggcc gccgcccgaa    10380
acgatccgac agcgcgccca gcacaggtgc gcaggcaaat tgcaccaacg catacagcgc    10440
cagcagaatg ccatagtggg cggtgacgtc gttcgagtga accagatcgc gcaggaggcc    10500
cggcagcacc ggcataatca ggccgatgcc gacagcgtcg agcgcgacag tgctcagaat    10560
tacgatcagg ggtatgttgg gtttcacgtc tggcctccgg accagcctcc gctggtccga    10620
ttgaacgcgc ggattctttta tcactgataa gttggtggac atattatgtt tatcagtgat    10680
aaagtgtcaa gcatgacaaa gttgcagccg aatacagtga tccgtgccgc cctggacctg    10740
ttgaacgagg tcggcgtaga cggtctgacg acacgcaaac tggcggaacg gttggggggtt    10800
cagcagccgg cgctttactg gcacttcagg aacaagcggg cgctgctcga cgcactggcc    10860
gaagccatgc tggcggagaa tcatacgcat tcggtgccga gagccgacga cgactggcgc    10920
tcatttctga tcgggaatgc ccgcagcttc aggcaggcgc tgctcgccta ccgcgatggc    10980
gcgcgcatcc atgccggcac gcgaccgggc gcaccgcaga tggaaacggc cgacgcgcag    11040
cttcgcttcc tctgcgaggc gggttttttcg gccggggacg ccgtcaatgc gctgatgaca    11100
atcagctact tcactgttgg ggccgtgctt gaggagcagg ccggcgacag cgatgccggc    11160
gagcgcggcg gcaccgttga acaggctccg ctctcgccgc tgttgcgggc gcgatagac    11220
gccttcgacg aagccggtcc ggacgcagcg ttcgagcagg gactcgcggt gattgtcgat    11280
```

-continued

```
ggattggcga aaaggaggct cgttgtcagg aacgttgaag gaccgagaaa gggtgacgat    11340
tgatacagag ccgggtttgt cacccgtata agctgaagca ggcacaaatc agggaaataa    11400
acaaaatccc gcatcccggg ataaagaaaa atcagggaat taatggcctg atggatttcc    11460
cgtggcgtcg aaagtgcggc accataggta tcagtcaccg cgatgagatc ccttaccatt    11520
ccagagtctg gcggttgatt attaatttgc tgatatagag cctcagcccg ctggc         11575
```

<210> SEQ ID NO 6
<211> LENGTH: 1632
<212> TYPE: DNA
<213> ORGANISM: Mentha spicata

<400> SEQUENCE: 6

```
atgagacgat ccggaaacta caaccctttct cgttgggatg tcaacttcat ccaatcgctt      60
ctcagtgact ataaggagga caaacacgtg attagggctt ctgagctggt cactttggtg     120
aagatggaac tggagaaaga aacgatcaa attcgacaac ttgagttgat cgatgacttg      180
cagaggatgg ggctgtccga tcatttccaa aatgagttca agaaatctt gtcctctata      240 tatctcgacc atcactatta caagaaccct tttccaaaag aagaaaggga tctctactcc     300
acatctcttg catttaggct cctcagagaa catggttttc aagtcgcaca agaggtattc     360
gatagtttca gaacgagga gggtgagttc aagaaagcc ttagcgacga caccagagga      420
ttgttgcaac tgtatgaagc ttcctttctg ttgacggaag gcgaaaccac gctcgagtca     480
gcgagggaat tcgccaccaa attttttggag gaaaaagtga cgagggtgg tgttgatggc    540 gacctttaa caagaatcgc atattctttg gacatccctc ttcattggag gattaaaagg      600
ccaaatgcac ctgtgtggat cgaatggtat aggaagaggc ccgacatgaa tccagtagtg   660
ttggagcttg ccatactcga cttaaatatt gttcaagcac aatttcaaga agagctcaaa   720
gaatccttca ggtggtggag aaatactggg tttgttgaga agctgccctt cgcaagggat    780
agactggtgg aatgctactt ttggaatact gggatcatcg agccacgtca gcatgcaagt    840
gcaaggataa tgatgggcaa agtcaacgct ctgattacgg tgatcgatga tatttatgat    900
gtctatggca ccttagaaga actcgaacaa ttcactgacc tcattcgaag atgggatata   960
aactcaatcg accaacttcc cgattacatg caactgtgct tcttgcact caacaacttc     1020 gtcgatgata tcatcgtacga tgttatgaag gagaaaggcg tcaacgttat accctacctg   1080
cggcaatcgt gggttgattt ggcggataag tatatggtag aggcacggtg gttctacggc    1140
gggcacaaac caagtttgga agagtatttg gagaactcat ggcagtcgat aagtgggccc   1200
tgtatgttaa cgcacatatt cttccgagta acagattcgt tcacaaagga gaccgtcgac   1260
agtttgtaca aataccacga tttagttcgt tggtcatcct tcgttctgcg gcttgctgat   1320
gatttgggaa cctcggtgga agaggtgagc agagggatg tgccgaaatc acttcagtgc    1380
tacatgagtg actacaatgc atcggaggcg gaggcgcgga agcacgtgaa atggctgata   1440
gcggaggtgt ggaagaagat gaatgcggag agggtgtcga aggattctcc attcggcaaa   1500
gattttatag gatgtgcagt tgatttagga aggatgcgc agttgatgta ccataatgga   1560
gatgggcacg gcacacaaca ccctattata catcaacaaa tgaccagaac cttattcgag    1620
ccctttgcat ga                                                        1632
```

<210> SEQ ID NO 7
<211> LENGTH: 543
<212> TYPE: PRT
<213> ORGANISM: Mentha spicata

```
<400> SEQUENCE: 7

Met Arg Arg Ser Gly Asn Tyr Asn Pro Ser Arg Trp Asp Val Asn Phe
1               5                   10                  15

Ile Gln Ser Leu Leu Ser Asp Tyr Lys Glu Asp Lys His Val Ile Arg
            20                  25                  30

Ala Ser Glu Leu Val Thr Leu Val Lys Met Glu Leu Glu Lys Glu Thr
        35                  40                  45

Asp Gln Ile Arg Gln Leu Glu Leu Ile Asp Asp Leu Gln Arg Met Gly
    50                  55                  60

Leu Ser Asp His Phe Gln Asn Glu Phe Lys Glu Ile Leu Ser Ser Ile
65                  70                  75                  80

Tyr Leu Asp His His Tyr Tyr Lys Asn Pro Phe Pro Lys Glu Glu Arg
                85                  90                  95

Asp Leu Tyr Ser Thr Ser Leu Ala Phe Arg Leu Leu Arg Glu His Gly
            100                 105                 110

Phe Gln Val Ala Gln Glu Val Phe Asp Ser Phe Lys Asn Glu Glu Gly
        115                 120                 125

Glu Phe Lys Glu Ser Leu Ser Asp Asp Thr Arg Gly Leu Leu Gln Leu
    130                 135                 140

Tyr Glu Ala Ser Phe Leu Leu Thr Glu Gly Glu Thr Thr Leu Glu Ser
145                 150                 155                 160

Ala Arg Glu Phe Ala Thr Lys Phe Leu Glu Glu Lys Val Asn Glu Gly
                165                 170                 175

Gly Val Asp Gly Asp Leu Leu Thr Arg Ile Ala Tyr Ser Leu Asp Ile
            180                 185                 190

Pro Leu His Trp Arg Ile Lys Arg Pro Asn Ala Pro Val Trp Ile Glu
        195                 200                 205

Trp Tyr Arg Lys Arg Pro Asp Met Asn Pro Val Val Leu Glu Leu Ala
    210                 215                 220

Ile Leu Asp Leu Asn Ile Val Gln Ala Gln Phe Gln Glu Glu Leu Lys
225                 230                 235                 240

Glu Ser Phe Arg Trp Trp Arg Asn Thr Gly Phe Val Glu Lys Leu Pro
                245                 250                 255

Phe Ala Arg Asp Arg Leu Val Glu Cys Tyr Phe Trp Asn Thr Gly Ile
            260                 265                 270

Ile Glu Pro Arg Gln His Ala Ser Ala Arg Ile Met Met Gly Lys Val
        275                 280                 285

Asn Ala Leu Ile Thr Val Ile Asp Asp Ile Tyr Asp Val Tyr Gly Thr
    290                 295                 300

Leu Glu Glu Leu Glu Gln Phe Thr Asp Leu Ile Arg Arg Trp Asp Ile
305                 310                 315                 320

Asn Ser Ile Asp Gln Leu Pro Asp Tyr Met Gln Leu Cys Phe Leu Ala
                325                 330                 335

Leu Asn Asn Phe Val Asp Asp Thr Ser Tyr Asp Val Met Lys Glu Lys
            340                 345                 350

Gly Val Asn Val Ile Pro Tyr Leu Arg Gln Ser Trp Val Asp Leu Ala
        355                 360                 365

Asp Lys Tyr Met Val Glu Ala Arg Trp Phe Tyr Gly Gly His Lys Pro
    370                 375                 380

Ser Leu Glu Glu Tyr Leu Glu Asn Ser Trp Gln Ser Ile Ser Gly Pro
385                 390                 395                 400

Cys Met Leu Thr His Ile Phe Phe Arg Val Thr Asp Ser Phe Thr Lys
```

-continued

```
                405                 410                 415

Glu Thr Val Asp Ser Leu Tyr Lys Tyr His Asp Leu Val Arg Trp Ser
            420                 425                 430

Ser Phe Val Leu Arg Leu Ala Asp Asp Leu Gly Thr Ser Val Glu Glu
        435                 440                 445

Val Ser Arg Gly Asp Val Pro Lys Ser Leu Gln Cys Tyr Met Ser Asp
    450                 455                 460

Tyr Asn Ala Ser Glu Ala Glu Ala Arg Lys His Val Lys Trp Leu Ile
465                 470                 475                 480

Ala Glu Val Trp Lys Lys Met Asn Ala Glu Arg Val Ser Lys Asp Ser
            485                 490                 495

Pro Phe Gly Lys Asp Phe Ile Gly Cys Ala Val Asp Leu Gly Arg Met
            500                 505                 510

Ala Gln Leu Met Tyr His Asn Gly Asp Gly His Gly Thr Gln His Pro
        515                 520                 525

Ile Ile His Gln Gln Met Thr Arg Thr Leu Phe Glu Pro Phe Ala
    530                 535                 540
```

PRODUCTION OF CYCLIC TERPENOIDS

This application claims the benefit of U.S. Provisional Application No. 60/229,907, filed Sep. 1, 2000 and the benefit of U.S. Provisional Application No. 60/229,858 filed Sep. 1, 2000.

FIELD OF THE INVENTION

This invention is in the field of microbiology. More specifically, this invention pertains to methods for the production of cyclic terpenoid compounds in microbial hosts that metabolize single carbon substrates as a sole carbon source.

BACKGROUND OF THE INVENTION

Monoterpenes have value in the flavor and fragrance industries, as components in industrial solvents and in the pharmaceutical industry where selected compounds have shown promise as both chemopreventive and chemotheraputic agents for solid tumors.

Although found in a wide range of organisms, including bacteria, fungi, algae, insects and even higher animals such as alligators and beavers, monoterpenes are most widely produced by terrestrial plants such as components of flower scents, essential oils, and turpentine. One of the most common sources of the monoterpenes are the herbaceous plant and conifer turpentines. The pinene regioisomers (α-pinene, β-pinene) are 2 principal monoterpenes of turpentine as they serve as large volume aroma chemicals. Other essential oils (from orange, lime, lemon, and peppermint) are valued in flavoring and perfumery. The cyclization of linear terpenoid compounds to form cyclic derivatives may generate diverse aromatic structures with differing functionality.

At present the monoterpenes may be obtained either by extraction from natural sources or by chemical synthesis. Both processes are time consuming and expensive. Although small scale production of selected monoterpenes has been demonstrated in microbial hosts, a facile method for the production of monoterpenes on an industrial scale has yet to be reported. For example some monoterpene synthases have been successfully cloned and expressed in *Escherichia coli*. Specifically, limonene synthase, which catalyzes the cyclization of geranyldiphosphate to yield the olefin 4(S)-limonene in *Perilla frutescens* has been cloned into *Escherichia coli* and functionally expressed (Yuba et al. *Arch Biochem Biophys* 332:280–287, (1996)). Reports of microbial expression however have been limited to microbe traditionally used for fermentative production were grown on complex carbon substrates.

There are a number of microorganisms that utilize single carbon substrates as sole energy sources. These organisms are referred to as methylotrophs and herein as "C1 metabolizers". These organisms are characterized by the ability to use carbon substrates lacking carbon to carbon bonds as a sole source of energy and biomass. A subset of methylotrophs are the methanotrophs which have the unique ability to utilize methane as a sole energy source. Although a large number of these organisms are known, few of these microbes have been successfully harnessed to industrial processes for the synthesis of materials. Although single carbon substrates are cost effective energy sources, difficulty in genetic manipulation of these microorganisms as well as a dearth of information about their genetic machinery has limited their use primarily to the synthesis of native products. For example the commercial applications of biotransformation of methane have historically fallen broadly into three categories: 1) Production of single cell protein, (Sharpe D. H. BioProtein Manufacture 1989. Ellis Horwood series in applied science and industrial technology. New York: Halstead Press.) (Villadsen, John, *Recent Trends Chem. React. Eng.*, [Proc. Int. Chem. React. Eng. Conf.], 2nd (1987), Volume 2, 320–33. Editor(s): Kulkarni, B. D.; Mashelkar, R. A.; Sharma, M. M. Publisher: Wiley East., New Delhi, India; Naguib, M., Proc. OAPEC Symp. Petroprotein, [Pap.] (1980), Meeting Date 1979, 253–77 Publisher: Organ. Arab Pet. Exporting Countries, Kuwait, Kuwait.); 2) epoxidation of alkenes for production of chemicals (U.S. Pat. No. 4,348,476); and 3) biodegradation of chlorinated pollutants (Tsien et al., *Gas, Oil, Coal, Environ. Biotechnol.* 2, [Pap. Int. IGT Symp. *Gas, Oil, Coal, Environ. Biotechnol.*], 2nd (1990), 83–104. Editor(s): Akin, Cavit; Smith, Jared. Publisher: Inst. Gas Technol., Chicago, Ill.; WO 9633821; Merkley et al., *Biorem. Recalcitrant Org.*, [Pap. Int. In Situ On-Site Bioreclam. Symp.], 3rd (1995), 165–74. Editor(s): Hinchee, Robert E; Anderson, Daniel B.; Hoeppel, Ronald E. Publisher: Battelle Press, Columbus, Ohio: Meyer et al., *Microb. Releases* (1993), 2(1), 11–22). Even here, the commercial success of the methane biotransformation has been limited to epoxidation of alkenes due to low product yields, toxicity of products and the large amount of cell mass required to generate product associated with the process.

One of the most common classes of single carbon metabolizers are the methanotrophs. Methanotrophic bacteria are defined by their ability to use methane as a sole source of carbon and energy. Methane monooxygenase is the enzyme required for the primary step in methane activation and the product of this reaction is methanol (Murrell et al., *Arch. Microbiol.* (2000), 173(5–6), 325–332). This reaction occurs at ambient temperature and pressures whereas chemical transformation of methane to methanol requires temperatures of hundreds of degrees and high pressure (Grigoryan, E. A., *Kinet. Catal.* (1999), 40(3), 350–363; WO 2000007718; U.S. Pat. No. 5,750,821). It is this ability to transform methane under ambient conditions along with the abundance of methane that makes the biotransformation of methane a potentially unique and valuable process.

Many methanotrophs contain an inherent isoprenoid pathway which enables these organisms to synthesize other non-endogenous isoprenoid compounds. Since methanotrophs can use one carbon substrate (methane or methanol) as an energy source, it is possible to produce monoterpenes at low cost. Furthermore, during the fermentation, volatile compounds can be easily removed as methane is passed through fermentation media. It is also advantageous to produce via bio-route since many of monoterpenes have chirality and it is difficult to control the synthesis and purification of specific chirally active compound in chemical synthesis.

A need exists therefore for a method of production of highly valuable monoterpenes from an inexpensive feedstock. Applicants have solved the stated problem by providing a C1 metabolizing microorganism having transformed with a gene encoding a cyclic terpene synthase, having the ability to produce to a variety of monoterpenes.

SUMMARY OF THE INVENTION

The invention provides a method for the production of a monoterpene comprising:

a) providing a transformed C1 metabolizing host cell comprising:
  (i) suitable levels of geranyl pyrophosphate; and
  (ii) at least one isolated nucleic acid molecule encoding a cyclic terpene synthase under the control of suitable regulatory sequences;
b) contacting the host cell of step (a) under suitable growth conditions with an effective amount of a C1 carbon substrate whereby a monoterpene compound is produced.

Preferred single carbon substrates of the present invention include but are not limited to methane, methanol, formaldehyde, formic acid, methylated amines, methylated thiols, and carbon dioxide.

Preferred C1 metabolizers or facultative methylotrophs where obligate methanotrophic bacteria are most preferred. Most preferred C1 metabolizers are those obligate methanotrophs comprising a functional Embden-Meyerof carbon pathway, said pathway comprising a gene encoding a pyrophosphate dependent phosphofructokinase enzyme.

Preferred cyclic terpene synthases of the invention include but are not limited to limonene synthase, pinene synthase, bornyl synthase, phellandrene synthase, cineole synthase, and sabinene synthase.

In an alternate embodiment the invention provides for the expression of upper pathway isoprenoid genes for the donwstream produciton of monoterpenes, the upper pathway isoprenoid genes selected from the group consisting of D-1-deoxyxylulose-5-phosphate synthase (DXS); D-1-deoxyxylulose-5-phosphate reductoisomerase (DXR); 2C-methyl-d-erythritol cytidylyltransferase (IspD), 4-diphosphocytidyl-2-C-methylerythritol kinase (IspE), 2C-methyl-d-erythritol 2,4-cyclodiphosphate synthase (IspF), CTP synthase (IspA) and Geranyltranstransferase (PyrG).

BRIEF DESCRIPTION OF THE DRAWINGS, SEQUENCE DESCRIPTIONS, AND BIOLOGICAL DEPOSITS

The invention can be more fully understood from the following detailed description and the accompanying sequence descriptions, which form a part of this application.

The following sequences comply with 37 C.F.R. 1.821–1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

SEQ ID NO:1–4 are primer sequences.

SEQ ID NO:5 is the nucleotide sequence of plasmid pTJS75:dxS:dxR:Tn5Kn.

SEQ ID NO:6 is the nucleotide sequence of limonene synthase gene from *Mentha spicata* with 57 amino acid sequences deleted from N-terminal.

SEQ ID NO:7 is deduced amino acid sequence of limonene synthase gene used in SEQ ID NO:6.

Applicants made the following biological deposits under the terms of the Budapest Treaty on the International Recognition of the Deposit of Micro-organisms for the Purposes of Patent Procedure:

| Depositor Identification Reference | International Depository Designation | Date of Deposit |
| --- | --- | --- |
| Methylomonas 16a | ATCC PTA 2402 | Aug. 21, 2000 |

DETAILED DESCRIPTION OF THE INVENTION

The present invention describes a method for the synthesis of monoterpenes in a recombinant methylotrophic or methanotrophic host. Monoterpenes are used in flavors and fragrances, coatings and nutrition and health applications.

The following definitions may be used for interpretation of the claims and the specification.

"Open reading frame" is abbreviated ORF.

"Polymerase chain reaction" is abbreviated PCR.

The term "isoprenoid" or "terpenoid" refers to the compounds or any molecule derived from the isoprenoid pathway including 10 carbon terpenoids (monoterpene) and their derivatives, such as limonene, pinene, sabinene, β-phellandrene, borneol, carotenoids and xanthophylls.

The term "isoprene subunit" refers to a basic 5 carbon unit of isopentenyl diphosphate that further condenses to form a terpenoid.

The term "cyclic terpene synthase" refers to an enzyme capable of using geranyl pyrophosphate as a substrate to produce a cyclic terpenoid compound.

Figure 3A:
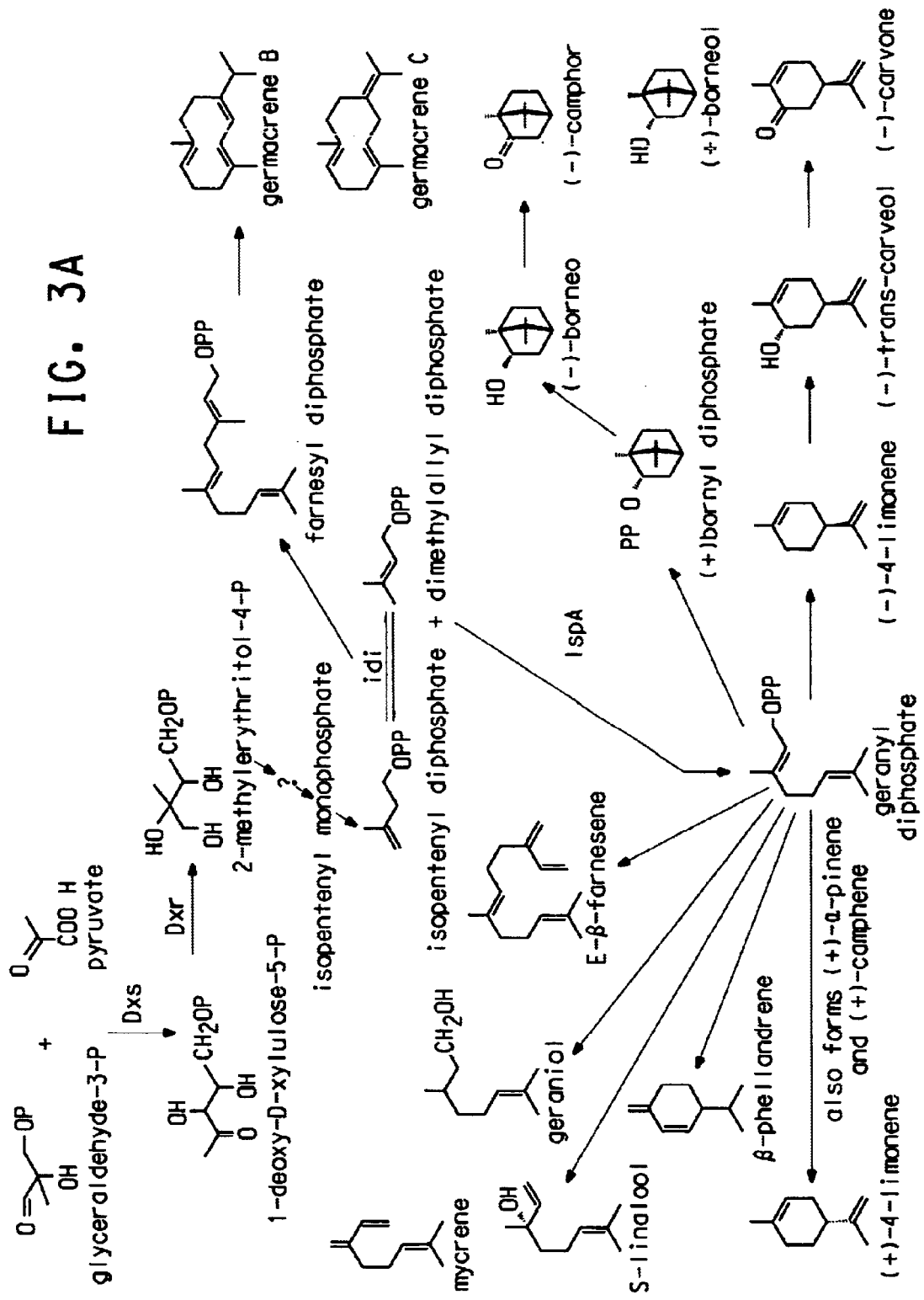
FIG. 3 shows the examples of monoterpenes derived from geranyl diphosphate.
Figure 3B:
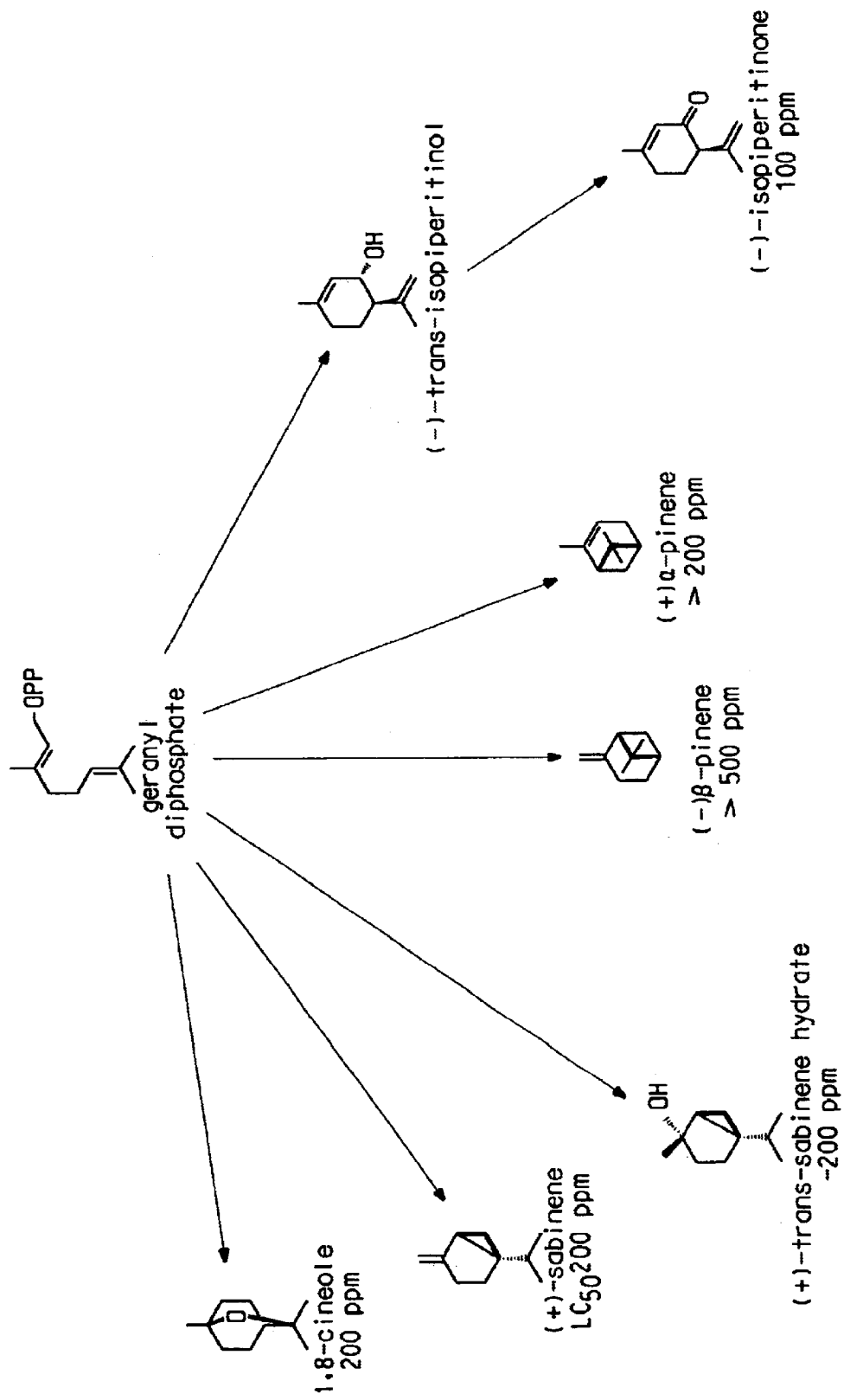

The term "monoterpene" refers to any 10 carbon compound derived from geranyl pyrophosphate or its derivatives built upon 2 isoprene subunits (see FIG. 3 for example).

The term "cyclic monoterpene" refers to a cyclic terpenoid derived from geranyl pyrophosphate having 10 carbon atoms.

The term "limonene synthase" refers to enzyme that catalyzes the conversion of geranyl pyrophosphate to (−)-Limonene.

The term "pinene synthase" refers to the enzyme that catalyzes the conversion of geranyl pyrophosphate to pinene.

The term "bornyl synthase" refers to the enzyme that catalyzes the conversion of geranyl pyrophosphate to borneol.

The term "phellandrene synthase" refers to the enzyme that catalyzes the conversion of geranyl pyrophosphate to β-phellandrene.

The term "cineole synthase" refers to the enzyme that catalyzes the conversion of geranyl pyrophosphate to cineole.

The term "sabinene synthase" refers to the enzyme that catalyzes the conversion of geranyl pyrophosphate to sabinene.

The term "geranyl diphosphate" and "geranyl pyrophosphate" will be used interchangeably and will refer to a compound having the general formula

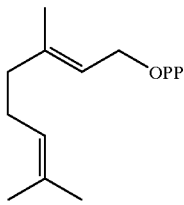

The term "Dxs" refers to the 1-deoxyxylulose-5-phosphate synthase enzyme encoded by the dxs gene.

The term "Dxr" refers to the 1-deoxyxylulose-5-phosphate reductoisomerase enzyme encoded by the dxr gene.

The term "YgbP" or "IspD" refers to the 2C-methyl-D-erythritol cytidyltransferase enzyme encoded by the ygbP or ispD gene. The names of the gene, ygbP or ispD, are used interchangeably in this application. The names of gene product, YgbP or IspD are used interchangeably in this application.

The term "YchB" or "IspE" refers to the 4-diphosphocytidyl-2-C-methylerythritol kinase enzyme encoded by the ychB or ispE gene. The names of the gene, ychB or ispE, are used interchangeably in this application. The names of gene product, YchB or IspE are used interchangeably in this application.

The term "YgbB" or "IspF" refers to the 2C-methyl-d-erythritol 2,4-cyclodiphosphate synthase enzyme encoded by the ygbB or ispF gene. The names of the gene, ygbB or ispF, are used interchangeably in this application. The names of gene product, YgbB or IspF are used interchangeably in this application.

The term "PyrG" refers to a CTP synthase enzyme encoded by the pyrG gene.

The term "IspA" refers to Geranyltransferase or farnesyl diphosphate synthase enzyme as one of prenyl transferase family encoded by ispA gene.

The term "LytB" refers to protein having a role in the formation of dimethylallyl-pyrophosphate in the isoprenoiod pathway and which is encoded by lytB gene.

The term "upper pathway isoprene genes" refers to any of the following genes and gene products associated with the isoprenoid biosynthetic pathway including the dxs gene (encoding 1-deoxyxylulose-5-phosphate synthase), the dxr gene (encoding 1-deoxyxylulose-5-phosphate reductoisomerase), the "ispD" gene (encoding the 2C-methyl-D-erythritol cytidyltransferase enzyme; the "ispE" gene (encoding the 4-diphosphocytidyl-2-C-methylerythritol kinase; the "ispF" gene (encoding a 2C-methyl-d-erythritol 2,4-cyclodiphosphate synthase the "pyrG" gene (encoding a CTP synthase); the "ispA" gene (encoding geranyltransferase or farneseyl diphosphate synthase), and the "lytB" gene.

The term "single carbon substrate" refers to a carbon substrate useful as a microbial feedstock being devoid of carbon to carbon bonds.

The term "C1 metabolizer" refers to a microorganism that has the ability to use an single carbon substrate as a sole source of energy and biomass. C1 metabolizers will typically be methylotrophs and/or methanotrophs.

The term "methylotroph" means an organism capable of oxidizing organic compounds which do not contain carbon-carbon bonds. Where the methylotroph is able to oxidize CH4, the methylotroph is also a methanotroph.

The term "methanotroph" means a prokaryote capable of utilizing methane as a substrate. Complete oxidation of methane to carbon dioxide occurs by aerobic degradation pathways. Typical examples of methanotrophs useful in the present invention include but are not limited to the genera *Methylomonas, Methylobacter Methylococcus,* and *Methylosinus.*

The term "*Methylomonas* 16a" and "*Methylomonas* 16a sp." are used interchangeably and refer to the *Methylomonas* strain used in the present invention.

The term "Embden-Meyerhof pathway" refers to the series of biochemical reactions for conversion of hexoses such as glucose and fructose to important cellular 3 carbon intermediates such as glyceraldehyde 3 phosphate, dihydroxyacetone phosphate, phosphoenol pyruvate and pyruvate. These reactions typically proceed with net yield of biochemically useful energy in the form of ATP. The key enzymes unique to the Embden-Meyerof pathway are the phosphofructokinase and fructose 1,6 bisphosphate aldolase.

The term "Entner-Douderoff pathway" refers to a series of biochemical reactions for conversion of hexoses suchas as glucose or fructose to important 3 carbon cellular intermediates pyruvate and glyceraldehyde 3 phosphate without any net production of biochemically useful energy. The key enzymes unique to the Entner-Douderoff pathway are the 6 phosphogluconate dehydratase and the ketodeoxyphosphogluconate aldolase.

The term "high growth methanotrophic bacterial strain" refers to a bacterium capable of growth with methane or methanol as sole carbon and energy source which possess a functional Embden-Meyerof carbon flux pathway resulting in a high rate of growth and yield of cell mass per gram of C1 substrate metabolized. The specific "high growth methanotrophic bacterial strain" described herein is referred to as "*Methylomonas* 16a" or "16a", which terms are used interchangeably.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

"Gene" refers to a nucleic acid fragment that is capable of being expressed as a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitates transformation of a particular host cell. "Expression cassette" refers to a specific vector containing a foreign gene and having elements in addition to the foreign gene that allow for enhanced expression of that gene in a foreign host.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

The present invention provides a method for the synthesis of monoterpenes in a methylotrophic or methanotrophic microbial host. Typical monoterpenes of the invention are those that are derived from geranyl pyrophosphate and contain ten carbon atoms. Typically the hosts have the elements of the isoprenoid pathway that will result in the production of geranyl pyrophosphate. The microbial host will also comprise a gene encoding a synthase, which is capable of using geranyl pyrophosphate as a substrate to produce a monoterpene.

Identification and Isolation of C1 Metabolizing Microorganisms

The present invention provides for the expression of cyclic terpene synthases in microorganisms which are able to use single carbon substrates as a sole energy source. Such microorganisms are referred to herein as C1 metabolizers. The host microorganism may be any C1 metabolizer which has the ability to synthesize geranyl diphosphate (GPP), the precursor for many of the monoterpenes.

Many C1 metabolizing microorganisms are known in the art and are able to use a variety of single carbon substrates. Single carbon substrates useful in the present invention include but are not limited to methane, methanol, formaldehyde, formic acid, methylated amines (e.g. mono, di- and tri-methyle amine), methylated thiols, and carbon dioxide.

All C1 metabolizing microorganisms are generally classed as methylotrophs. Methylotrophs may be defined as any organism capable of oxidizing organic compounds which do not contain carbon-carbon bonds. A subset of methylotrophs are the methanotrophs which have the distinctive ability to oxidize methane. Facultative methylotrophs have the ability to oxidize organic compounds which do not contain carbon-carbon bonds, but may also use other carbon substrates such as sugars and complex carbohydrates for energy and biomass. Obligate methylotrophs are those organisms which are limited to the use of organic compounds which do not contain carbon-carbon bonds for the generation of energy and obligate methanotrophs are those obligate methylotrophs that have the ability to oxidize methane.

Facultative methylotrophic bacteria are found in many environments, but are isolated most commonly from soil, landfill and waste treatment sites. Many facultative methylotrophs are members of the β, and γ subgroups of the Proteobacteria (Hanson et al., *Microb. Growth C1 Compounds.*, [Int. Symp.], 7th (1993), 285–302. Editor(s): Murrell, J. Collin; Kelly, Don P. Publisher: Intercept, Andover, UK; Madigan et al., *Brock Biology of Microorganisms*, 8th edition, Prentice Hall, UpperSaddle River, N.J. (1997)). Facultative methylotrophic bacteria suitable in the present invention include but are not limited to,

*Methylophilus, Methylobacillus, Methylobacterium, Hyphomicrobium, Xanthobacter, Bacillus, Paracoccus, Nocardia, Arthrobacter, Rhodopseudomonas,* and *Pseudomonas*.

The ability to utilize single carbon substrates is not limited to bacteria, but also extends to yeasts and fungi. For example a variety of yeast genera are able to use single carbon substrates in addition to more complex materials as energy sources. Specific methylotrophic yeasts useful in the present invention include but are not limited to *Candida, Hansenula, Pichia, Torulopsis,* and *Rhodotorula*.

Those methylotrophs having the additional ability to utilize methane are referred to as methanotrophs. Of interest in the present invention are those obligate methanotrophs which are methane utilizers but which are obliged to use organic compounds lacking carbon-carbon bonds. Exemplary of these organisms are included in, but not limited to the genera *Methylomonas, Methylobacter, Mehtylococcus, Methylosinus, Methylocyctis, Methylomicrobium,* and *Methanomonas*.

Of particular interest in the present invention are high growth obligate methanotrophs having an energetically favorable carbon flux pathway. For example Applicants have discovered a specific strain of methanotroph having several pathway features which make it particularly useful for carbon flux manipulation. This type of strain has served as the host in present application and is known as *Methylomonas* 16a (ATCC PTA 2402).

The present strain contains several anomalies in the carbon utilization pathway. For example, based on genome sequence data, the strain is shown to contain genes for two pathways of hexose metabolism. The Entner-Douderoff Pathway which utilizes the keto-deoxy phosphogluconate aldolase enzyme is present in the strain. Is generally well accepted that this is the operative pathway in obligate methanotrophs. Also present, however, is the Embden-Meyerhoff Pathway which utilizes the Fructose bisphosphate aldolase enzyme. It is well known that this pathway is either not present or not operative in obligate methanotrophs. Energetically, the latter pathway is most favorable and allows greater yield of biologically useful energy and ultimately production of cell mass and other cell mass-dependent products in *Methylomonas* 16a. The activity of this pathway in the present 16a strain has been confirmed through microarray data and biochemical evidence measuring the reduction of ATP. Although the 16a strain has been shown to possess both the Embden-Meyerhoff and the Entner-Douderoff pathway enzymes the data suggests that the Embden-Meyerhoff pathway enzymes are more strongly expressed than the Entner-Douderoff pathway enzymes. This result is surprising and counter to existing beliefs on the glycolytic metabolism of methanotrophic bacteria. Applicants have discovered other methanotrophic bacteria having this characteristic, including for example, *Methylomonas clara* and *Methylosinus sporium*.

A particularly novel and useful feature of the Embden-Meyerhoff pathway in strain 16a is that the key phosphofructokinase step is pyrophosphate dependent instead of ATP dependent. This feature adds to the energy yield of the pathway by using pyrophosphate instead of ATP. Because of it's significance in providing an energetic advantage to the strain this gene in the carbon flux pathway is considered diagnostic for the present strain.

In methanotrophic bacteria methane is converted to biomolecules via a cyclic set of reaction known as the ribulose monophosphate pathway or RuMP cycle. This pathway is comprised of three phases, each phases being a series of enzymatic steps (FIG. 3). The first step is "fixation" or incorporation of C-1 (formaldehyde) into a pentose to form a hexose or six carbon sugar. This occurs via a condensation reaction between a 5 carbon sugar (pentose) and formaldehyde and is catalyzed by hexulose monophosphate synthase. The second phase is termed "cleavage" and results in splitting of that hexose into two 3 carbon molecules. One of those three carbon molecules is recycled back through the RuMP pathway and the other 3 carbon fragment is utilized for cell growth. In methanotrophs and methylotrophs the RuMP pathway may occur as one of three variants. However only two of these variants are commonly found. The FBP/TA (fructose bisphosphotase/Transaldolase) or the KDPG/TA (keto deoxy phosphogluconate/transaldolase) pathway. (Dijkhuizen L., G. E. Devries. The Physiology and biochemistry of aerobic methanol-utilizing gram negative and gram positive bacteria. In: Methane and Methanol Utilizers 1992, ed Colin Murrell and Howard Dalton Plenum Press N.Y.).

The present strain is unique in the way it handles the "cleavage" steps where genes were found that carry out this conversion via fructose bisphosphate as a key intermediate. The genes for fructose bisphosphate aldolase and transaldolase were found clustered together on one piece of DNA. Secondly the genes for the other variant involving the keto deoxy phosphogluconate intermediate were also found clustered together. Available literature teaches that these organisms (methylotrophs and methanotrophs) rely solely on the KDPG pathway and that the FBP-dependent fixation pathway is utilized by facultative methylotrophs (Dijkhuizen et al., supra). Therefore the latter observation is expected whereas the former is not. The finding of the FBP genes in and obligate methane utilizing bacterium is both surprising and suggestive of utility. The FBP pathway is energetically favorable to the host microorganism due to the fact that less energy (ATP) is utilized than is utilized in the KDPG pathway. Thus organisms that utilize the FBP pathway may have an energetic advantage and growth advantage over those that utilize the KDPG pathway. This advantage may also be useful for energy-requiring production pathways in the strain. By using this pathway a methane-utilizing bacterium may have an advantage over other methane utilizing organisms as production platforms for either single cell protein or for any other product derived from the flow of carbon through the RuMP pathway.

Accordingly the present invention provides a method for the production of a monoterpene compound comprising providing a transformed C1 metabolizing host cell which
(a) grows on a C1 carbon substrate selected from the group consisting of methane and methanol; and
(b) comprises a functional Embden-Meyeroff carbon pathway, said pathway comprising a gene encoding a pyrophosphate dependent phosphofructokinase enzyme; and
(c) contains an endogenouse source of geranyl diphosphate (GPP)

Isolation of C1 Metabolizing Microorganisms

The C1 metabolizing microorganisms of the present invention are ubiquitous and many have been isolated and characterized. A general scheme for isolation of these strains includes addition of an inoculum into a sealed liquid mineral salts media, containing either methane or methanol. Care must be made of the volume:gas ratio and cultures are typically incubated between 25–55° C. Typically, a variety of different methylotrophic bacteria can be isolated from a first enrichment, if it is plated or streaked onto solid media when growth is first visible. Methods for the isolation of methanotrophs are common and well known in the art (See for example Thomas D. Brock in Biotechnology: *A Textbook of Industrial Microbiology*, Second Edition (1989) Sinauer Associates, Inc., Sunderland, Mass.; Deshpande, Mukund V., *Appl. Biochem. Biotechnol*, 36: 227 (1992); or Hanson, R. S. et al. *The Prokaryotes: a handbook on habitats, isolation, and identification of bacteria*; Springer-Verlag: Berlin, N.Y., 1981; Volume 2, Chapter 118).

As noted above, preferred C1 metabolizer is one that incorporates an active Embden-Meyerhoff pathway as indicated by the presence of a pyrophosphate dependent phosphofructokinase. It is contemplated that the present teaching will enable the general identification and isolation of similar strains. For example, the key characteristics of the present high growth strain are that it is an obligate methanotroph, using only either methane of methanol as a sole carbon source and possesses a functional Embden-Meyerhoff, and particularly a gene encoding a pyrophosphate dependent phosphofructokinase. Methods for the isolation of methanotrophs are common and well known in the art (See for example Thomas D. Brock supra or Deshpande, supra). Similarly, pyrophosphate dependent phosphofructokinase has been well characterized in mammalian systems and assay methods have been well developed (see for example Schliselfeld et al. *Clin. Biochem.* (1996), 29(1), 79–83; Clark et al., *J. Mol. Cell. Cardiol*. (1980), 12(10), 1053–64. The contemporary microbiologist will be able to use these techniques to identify the present high growth strain.

Genes Involved in Monoterpene Synthesis

Many C1 metabolizing strains possess the ability to produce geranyl diphosphate (GPP) which is the substrate for monoterpene synthases. Where a host cell is employed that makes GPP it will only be necessary to introduce the specific terpene synthase for the production of a specific monoterpene.

Many cyclic terpene synthases are known in the art and any one will be suitable for expression in the hosts of the present invention. Limonene synthase is the most well characterized having been isolated from a variety of organisms including *Perilla frutescens* (Genbank Acc #AF317695), *Arabidopsis* (Genbank Acc # AB005235), *Perllia citriodora* (Genbank Acc # AF241790), *Schizonepeta tenuifolia* (Genbank Acc # AF233894), *Abies grandis* (Genbank Acc # AF139207), *Mentha longifolia* (Genbank Acc # AF175323) and *Mentha spicata* (Genbank Acc # L13459). Any one of the known genes encoding limonene synthase may be used for expression in the present invention where genes isolated form and *Mentha spicata* are preferred.

Other cyclic terpene synthases are known. For example bornyl diphosphate synthase has been isolated from *Salvia officinalis* (Genbank Acc # AF051900); 1,8-cineole synthase has been isolated from *Salvia officinalis* (Genbank Acc # AF051899); phellandrene synthase has been isolated from *Abies grandis* (Genbank Acc # AF139205); sabinene synthase has been isolated from *Salvia officinalis* (Genbank Acc # AF051901); and pinene synthase has been isolated from *Artemisia annua* (Genbank Acc # AF276072), and *Abies grandis* (Genbank Acc # U87909).

Accordingly, suitable synthases for monoterpene expression include but not limited to limonene synthase, pinene synthase, bornyl synthase, phellandrene synthase, cineole synthase, and sabinene synthase.

It will be appreciated that where GPP is present in the host cell, expression of a specific terpene synthase will generate the corresponding monoterpene. So for example, the expression of limonene synthase will generate limonene, the expression of pinene synthase will generate pinene, the expression of sabinene synthase will generate sabinene, the expression of phellandrene synthase will generate β-phellandrene and the expression of bornyl diphosphate synthase will generate borneol (FIG. 3).

In some instances the specific C1 metabolizing host cell may be lacking some or all the elements of the pathway necessary for the production of geranyl diphosphate (GPP). Alternatively some of the elements of this pathway may be rate limiting and require overexpression for effective synthesis of GPP. In these situations it may be necessary to introduce some or all of the GPP synthetic pathway genes or "upper pathway isoprenoid genes" into the host, or to introduce additional copies of existing genes in the pathway to regulate or increase the production of certain rate limiting steps of the pathway. GPP is the end product of a biosynthetic pathway that begins with the condensation of Glyceraldehyde-3P and pyruvate and ends with the condensation of isopentenyl diphosphate (IPP) and dimethylallyl-diphosphate to form GPP (FIG. 3).

Figure 4A:
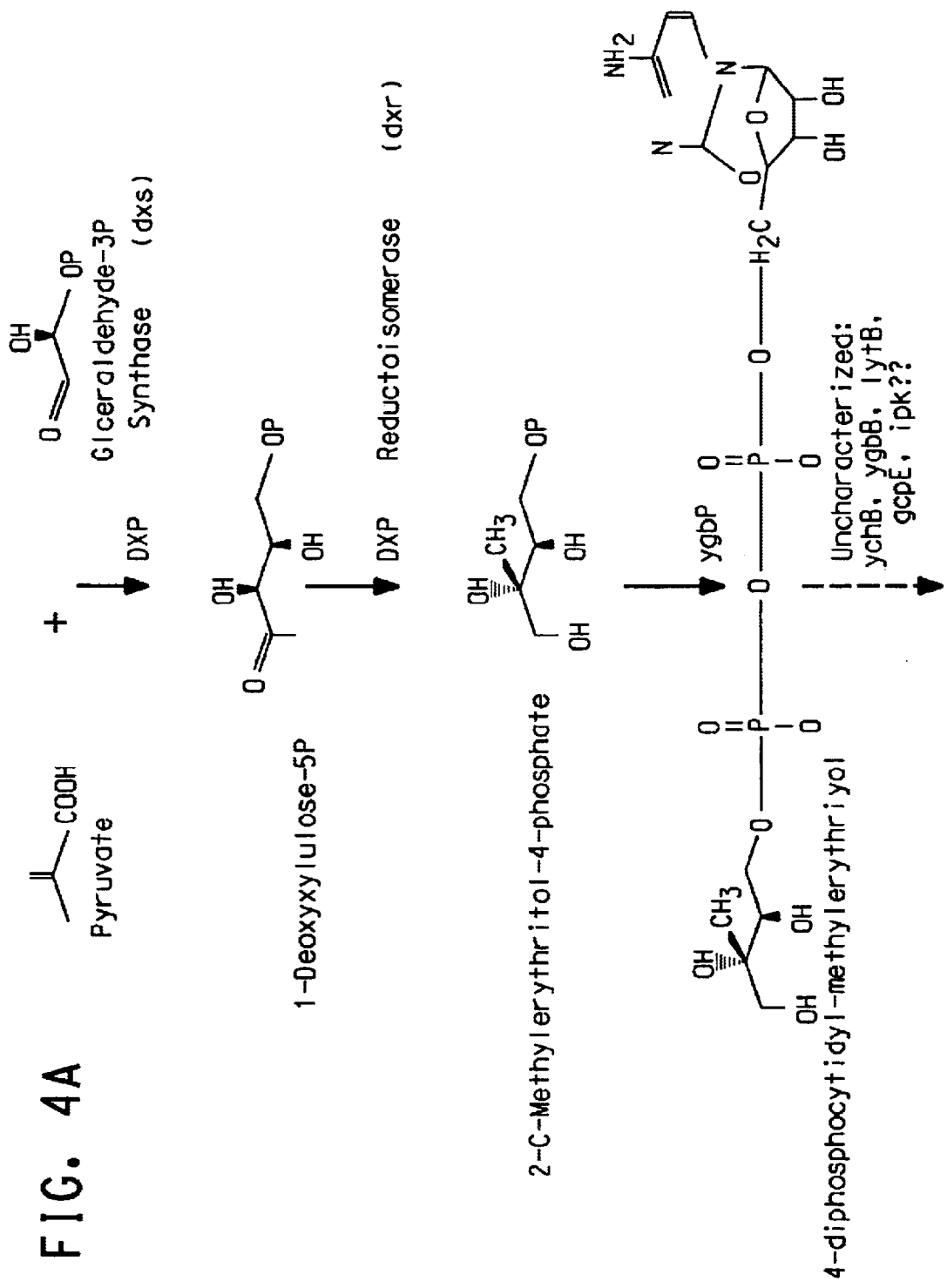
FIG. 4 illustrates the upper isoprenoid pathway.
Figure 4B:
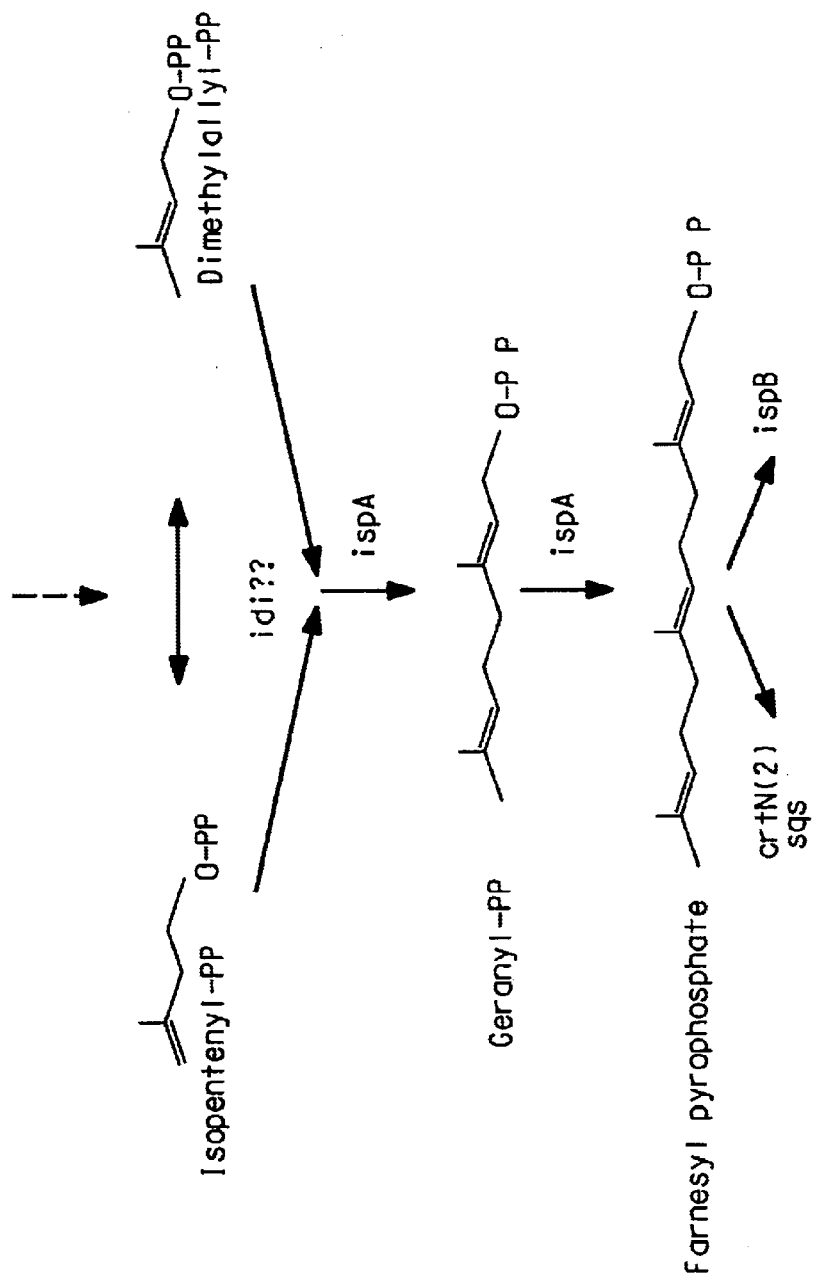

Many steps in isoprenoid pathways are known. For example, the initial steps of the alternate pathway involve the condensation of 2 carbons from pyruvate with C1 aldehyde group, D-glyceraldehyde 3-Phosphate to yield 5-carbon compound (D-1-deoxyxylulose-5-phosphate) (FIG. 3 and FIG. 4). Lois et al. has reported a gene, dxs, that encodes D-1-deoxyxylulose-5-phosphate synthase (DXS) that catalyzes the synthesis of D-1-deoxyxylulose-5-phosphate in *E. coli* (*Proc. Natl. Acad. Sci. USA* 95: 2105–2110 (1998).

Next, the isomerization and reduction of D-1-deoxyxylulose-5-phosphate yields 2-C-methyl-D-erythritol-4-phosphate. One of the enzymes involved in the isomerization and reduction process is D-1-deoxyxylulose-5-phosphate reductoisomerase (DXR). Takahashi et al. reported that dxr gene product catalyzes the formation of 2-C-methyl-D-erythritol-4-phosphate in the alternate pathway in *E. coli* (*Proc. Natl. Acad. Sci. USA* 95: 9879–9884 (1998)).

Steps converting 2-C-methyl-D-erythritol-4-phosphate to isopentenyl monophosphate are not well characterized although some steps are known. 2-C-methyl-D-erythritol-4-phosphate is then converted into 4-diphosphocytidyl-2C-methyl-D-erythritol in a CTP dependent reaction by the enzyme encoded by non-annotated gene ygbP. Rohdich et al. reported YgbP, a protein in *E. coli* that catalyzes the reaction mentioned above. Recently, ygbP gene was renamed as ispD as a part of isp gene cluster (SwissProt#Q46893) (*Proc. Natl. Acad. Sci. USA* 96:11758–11763 (1999)).

Then the 2 position hydroxy group of 4-diphosphocytidyl-2C-methyl-D-erythritol can be phosphorylated in an ATP dependent reaction by the enzyme encoded by ychB gene. Luttgen et al. has reported the presence of YchB protein in *E. coli* that phosphorylates 4-diphosphocytidyl-2C-methyl-D-erythritol resulting in 4-diphosphocytidyl-2C-methyl-D-erythritol 2-phosphate. Recently, ychB gene was renamed as ispE as a part of isp gene cluster (SwissProt#P24209) (Luttgen et al., *Proc. Natl. Acad. Sci. USA* 97:1062–1067 (2000)).

Herz et al. reported that ygbB gene product in *E. coli* converts 4-diphosphocytidyl-2C-methyl-D-erythritol 2-phosphate to 2C-methyl-D-erythritol 2,4-cyclodiphosphate. 2C-methyl-D-erythritol 2,4-cyclodiphosphate can be further converted into carotenoids in the carotenoid biosynthesis pathway (*Proc. Natl. Acad. Sci. USA* 97:2486–2490 (2000)). Recently, ygbB gene was renamed as ispF as a part of isp gene cluster (SwissProt #P36663).

The reaction catalyzed by YgbP enzyme is carried out in CTP dependent manner. Thus CTP synthase plays an important role in the isoprenoid pathway. PyrG encoded by pyrG gene in *E. coil* was determined to encode CTP synthase (Weng et al., *J. Biol. Chem.*, 261:5568–5574 (1986)).

Followed by the reactions not yet characterized, isopentenyl monophosphate is formed. Isopentenyl monophosphate is converted to isopentenyl diphosphate (IPP, C5) by isopentenyl monophosphate kinase encoded by ipk gene that is identical to the above mentioned yhcB (ispE) gene (Lange and Croteau, *Proc. Natl. Acad. Sci. USA* 96:13714–13719 (1999)). Isopentenyl diphosphate (IPP) is isomerized to dimethylallyl-pyrophosphate (DMAPP) by IPP:DMAPP isomerase (IPP isomerase, EC 5.3.3.2) or isopentenyl diphosphate isomerase (idi). Alternatively, recent evidence suggests that DMAPP can be formed separately at an earlier step of the mevalonate-independent pathway (Cunningham et al, *J. Bac.* 182 No. 20: 5841–5848(2000)), and that the enzyme encoded by lytB plays an essential role for this alternate route of DMAPP formation. DMAPP and IPP are condensed by geranyltranstransferase (ispA) gene (Ohto et al. *Plant Mol. Biol.* 40 (2), 307–321 (1999) to produce the linear C-10 compound geranyl diphosphate (GPP) which is the substrate for monoterpene synthases.

Accordingly, where it is necessary to regulate or install elements of the pathway needed for the synthesis of GPP in any C1 metabolizer, genes, known in the art, encoding the enzymes selected the group consisting of Dxs (1-deoxyxylulose-5-phosphate synthase), Dxr (1-deoxyxylulose-5-phosphate reductoisomerase), IspD (2C-methyl-D-erythritol cytidyltransferase), IspE (4-diphosphocytidyl-2-C-methylerythritol kinase), IspF, (2C-methyl-d-erythritol 2,4-cyclodiphosphate synthase), PyrG (CTP synthase), IspA (Geranyltransferase or farnesyl diphosphate synthase) and LytB may be used in the present C1 metabolizer host cell.

Construction of a Recombinant C1 Metabolizer for Monoterpene Production

Methods for introduction of genes encoding the appropriate cyclic terpene synthase into a suitable methylotrophic host are common. Microbial expression systems and expression vectors containing regulatory sequences suitable for expression of heterologus genes in methylotrophs are known. Any of these could be used to construct chimeric genes for expression of the any of the above mentioned cyclic terpene synthases. These chimeric genes could then be introduced into appropriate methylotrophic hosts via transformation to provide high level expression of the enzymes.

Vectors or cassettes useful for the transformation of suitable host cells are available. For example several classes of promoters may be used for the expression of genes encoding cyclic terpene synthases in methylotrophs and methanotrophs including, but not limited to endogenous promoters such as the deoxy-xylulose phosphate synthase, methanol dehydrogenase operon promoter (Springer et al. (1998) *FEMS Microbiol Lett* 160:119–124) the promoter for polyhydroxyalkanoic acid synthesis (Foellner et al. *Appl.Microbiol. Biotechnol.* (1993) 40:284–291), or promoters identified from native plasmid in methylotrophs (EP 296484) In addition to these native promoters non-native promoters may also be used, as for example the the promoter for lactose operon Plac (Toyama et al. *Microbiology* (1997) 143:595–602; EP 62971) or a hybrid promoter such as Ptrc (Brosius et al. (1984) *Gene* 27:161–172). Similarly promoters associated with antibiotic resistance e.g. kanamycin (Springer et al. (1998) *FEMS Microbiol Lett* 160:119–124; Ueda et al. *Appl. Environ. Microbiol.* (1991) 57:924–926) or tetracycline (U.S. Pat. No. 4,824,786) are also suitable.

Once the specific regulatory element is selected the promoter-gene cassette can be introduced into methylotrophs on a plasmid containing either a replicon (Brenner et al. *Antonie Van Leeuwenhoek* (1991) 60:43–48; Ueda et al. *Appl. Environ. Microbiol.* (1991) 57:924–926) for episomal expression or homologous regions for chromosomal integration (Naumov et al. *Mol. Genet. Mikrobiol. Virusol.* (1986) 11:44–48).

Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Where accumulation of a specific monoterpene is desired it may be necessary to reduce or eliminate the expression of certain genes in the target pathway or in competing pathways that may serve as competing sinks for energy or carbon. Methods of down-regulating genes for this purpose have been explored. Where sequence of the gene to be disrupted is known, one of the most effective methods gene down regulation is targeted gene disruption where foreign DNA is inserted into a structural gene so as to disrupt transcription. This can be effected by the creation of genetic cassettes comprising the DNA to be inserted (often a genetic marker) flanked by sequence having a high degree of homology to a portion of the gene to be disrupted. Introduction of the cassette into the host cell results in insertion of the foreign DNA into the structural gene via the native DNA replication mechanisms of the cell. (See for example Hamilton et al. (1989) *J. Bacteriol.* 171:4617–4622, Balbas et al. (1993) *Gene* 136:211–213, Gueldeneretal. (1996) *Nucleic Acids Res.* 24:2519–2524, and Smith et al. (1996) *Methods Mol. Cell. Biol.* 5:270–277.)

Antisense technology is another method of down regulating genes where the sequence of the target gene is known. To accomplish this, a nucleic acid segment from the desired gene is cloned and operably linked to a promoter such that the anti-sense strand of RNA will be transcribed. This construct is then introduced into the host cell and the antisense strand of RNA is produced. Antisense RNA inhibits gene expression by preventing the accumulation of mRNA which encodes the protein of interest. The person skilled in the art will know that special considerations are associated with the use of antisense technologies in order to reduce expression of particular genes. For example, the proper level of expression of antisense genes may require the use of different chimeric genes utilizing different regulatory elements known to the skilled artisan.

Although targeted gene disruption and antisense technology offer effective means of down regulating genes where the sequence is known, other less specific methodologies have been developed that are not sequence based. For example, cells may be exposed to a UV radiation and then screened for the desired phenotype. Mutagenesis with chemical agents is also effective for generating mutants and commonly used substances include chemicals that affect non-replicating DNA such as $HNO_2$ and $NH_2OH$, as well as agents that affect replicating DNA such as acridine dyes, notable for causing frameshift mutations. Specific methods for creating mutants using radiation or chemical agents are well documented in the art. See for example Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992).

Another non-specific method of gene disruption is the use of transposoable elements or transposons. Transposons are genetic elements that insert randomly in DNA but can be latter retrieved on the basis of sequence to determine where the insertion has occurred. Both in vivo and in vitro transposition methods are known. Both methods involve the use of a transposable element in combination with a transposase enzyme. When the transposable element or transposon, is contacted with a nucleic acid fragment in the presence of the transposase, the transposable element will randomly insert into the nucleic acid fragment. The technique is useful for random mutagenesis and for gene isolation, since the disrupted gene may be identified on the basis of the sequence of the transposable element. Kits for in vitro transposition are commercially available (see for example The Primer Island Transposition Kit, available from Perkin Elmer Applied Biosystems, Branchburg, N.J., based upon the yeast Ty1 element; The Genome Priming System, available from New England Biolabs, Beverly, Mass.; based upon the bacterial transposon Tn7; and the EZ::TN Transposon Insertion Systems, available from Epicentre Technologies, Madison, Wis., based upon the Tn5 bacterial transposable element.

In the context of the present invention the disruption of certain genes in the terpenoid pathway may enhance the accumulation of specific monoterpenes however, the decision of which genes to disrupt would need to be determined on an empirical basis. Candidate genes may include one or more of the prenyltransferase genes which, as described earlier, which catalyze the successive condensation of isopentenyl diphosphate resulting in the formation of prenyl diphosphates of various chain lengths (multiples of C-5 isoprene units). Other candidate genes for disruption would include any of those which encode proteins acting upon the terpenoid backbone prenyl diphosphates.

Industrial Production

Where commercial production of the instant proteins are desired a variety of culture methodologies may be applied. For example, large-scale production of a specific gene product, overexpressed from a recombinant microbial host may be produced by both batch or continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

Commercial production of the instant proteins may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Fermentation media in the present invention must contain suitable carbon substrates. The suitable carbon substrate may be one-carbon substrates such as methane or methanol for which metabolic conversion into key biochemical intermediates has been demonstrated. For example, methylotrophic yeast are known to utilize the carbon from methylamine to form trehalose or glycerol (Bellion et al., *Microb. Growth C1 Compd.*, [Int. Symp.], 7th (1993), 415–32. Editor(s): Murrell, J. Collin; Kelly, Don P. Publisher: Intercept, Andover, UK). Similarly, various species of *Candida* will metabolize alanine or oleic acid (Sulter et al., *Arch. Microbiol.* 153:485–489 (1990)). Hence it is contemplated that the source of carbon utilized in the present invention may encompass a wide variety of carbon containing substrates and will only be limited by the choice of organism.

Description of the Preferred Embodiments

*Methylomonas* 16a was isolated from a pond sediment using methane as sole source of carbon and energy. Among the colonies that were able to grow using methane as a sole source of carbon and energy, *Methylomonas* 16a strain was chosen for its rapid growth rate and pink pigmentation indicating inherent isoprenoid pathway for carotenoids.

The carbon flux pathways in *Methylomonas* 16a were analyzed by gene expression profiling and the presence and activity of the Embden-Meyerhoff pathway, comprising the presence of a functional pyrophosphate-linked phosphofructokinase enzyme as confirmed.

A truncated limonene synthase gene lacking the first 57 amino acids of the protein from *Mentha spicata* was obtained from pR58 plasmid. The truncated limonene synthase gene was cloned into the broad host vector pTJS75:dxS:dxR:Tn5Kn. The resulting plasmid pDH3 was transferred into *Methylomonas* 16a by triparental conjugal mating with fresh overnight cultures of *E. coli* helper pRK2013 and *E. coli* donor DH10B/pDH3.-Vector pTJS75:dxS:dxR:Tn5Kn was similarly transferred into *Methylomons*. Cloning methods and triparental conjugal mating are well known in the art. The presence of limonene synthase gene is verified using PCR.

The transformed culture of *Methylomonas* 16a was grown in airtight bottles to prevent the loss of volatile limonene compound. The compound produced by transformed *Methylomonas* 16a was extracted and analyzed by gas chromatography. The compound was confirmed to be limonene when compared to standard limonene. Approximately 0.5 ppm of limonene was detected from transformed culture.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual;* Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F. M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in Manual of Methods for General Bacteriology (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in Biotechnology: A Textbook of Industrial Microbiology, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "h" means hour(s), "min" means minute(s), "sec" means second(s), "d" means day(s), "mL" means milliliters, "L" means liters.

Microbial Cultivation and Preparation of Cell Suspensions, and Associated Analyses.

*Methylomonas* 16a is typically grown in serum stoppered Wheaton bottles using a gas/liquid ratio of at least 8:1 (i.e. 20 mL of Nitrate liquid media) media in a Wheaton bottle (Wheaton Scientific, Wheaton Ill.) of 160 mL total volume. The standard gas phase for cultivation contained 25% methane in air. These conditions comprise growth conditions and the cells are referred to as growing cells. In all cases the cultures were grown at 30° C. with constant shaking in a Lab-Line rotary shaker unless otherwise specified.

Cells obtained for experimental purposes were allowed to grow to maximum optical density (O.D. 660~1.0). Harvested cells were obtained by centrifugation in a Sorval RC-5B centrifuge using a SS-34 rotor at 6000 rpm for 20 min. These cell pellets were resuspended in 50 mM HEPES buffer pH 7. These cell suspensions are referred to as washed, resting cells.

Microbial growth was assessed in all experiments by measuring the optical density of the culture at 660 nm in an Ultrospec 2000 UV/Vis spectrophotometer (Pharmacia Biotech, Cambridge England) using a 1 cm light path cuvet. Alternatively microbial growth was assessed by harvesting cells from the culture medium by centrifugation as described above and resuspending the cells in distilled water with a second centrifugation to remove medium salts. The washed cells were then dried at 105° C. overnight in a drying oven for dry weight determination.

Methane concentration was determined as described by Emptage et al. (1997 *Env. Sci. Technol.* 31:732–734), hereby incorporated by reference.

Nitrate Medium for *Methylomonas* 16a

Nitrate liquid medium, also referred to herein as "defined medium" was comprised of various salts mixed with solution 1 as indicated below or where specified the nitrate was replaced with 15 mM ammonium chloride.

Solution 1 Composition for 100 fold concentrated stock solution of trace minerals.

|  | MW | Conc. (mM) | g per L |
|---|---|---|---|
| Nitriloacetic acid | 191.1 | 66.9 | 12.8 |
| $CuCl_2 \times 2H_2O$ | 170.48 | 0.15 | 0.0254 |
| $FeCl_2 \times 4H_2O$ | 198.81 | 1.5 | 0.3 |
| $MnCl_2 \times 4H_2O$ | 197.91 | 0.5 | 0.1 |
| $CoCl_2 \times 6H_2O$ | 237.9 | 1.31 | 0.312 |
| $ZnCl_2$ | 136.29 | 0.73 | 0.1 |
| $H_3BO_3$ | 61.83 | 0.16 | 0.01 |
| $Na_2MoO_4 \times 2H_2O$ | 241.95 | 0.04 | 0.01 |
| $NiCl_2 \times 6H_2O$ | 237.7 | 0.77 | 0.184 |

Mix the gram amounts designated above in 900 mL of $H_2O$, adjust to pH=7, and add $H_2O$ to an end volume of 1 L. Keep refrigerated.

Nitrate Liquid Medium

|  | MW | Conc. (mM) | g per L |
|---|---|---|---|
| $NaNO_3$ | 84.99 | 10 | 0.85 |
| $KH_2PO_4$ | 136.09 | 3.67 | 0.5 |

-continued

|  | MW | Conc. (mM) | g per L |
|---|---|---|---|
| Na$_2$SO$_4$ | 142.04 | 3.52 | 0.5 |
| MgCl$_2$ × 6H$_2$O | 203.3 | 0.98 | 0.2 |
| CaCl$_2$ × 2H$_2$O | 147.02 | 0.68 | 0.1 |
| 1 M HEPES (pH 7) | 238.3 |  | 50 mL |
| Solution 1 |  |  | 10 mL |

Dissolve in 900 mL H$_2$O. Adjust to pH = 7, and add H$_2$O to give 1 L. For agar plates: Add 15 g of agarose in 1 L of medium, autoclave, let cool down to 50°C., mix, and pour plates.

Nitrate and Nitrite Assays 1 mL samples of cell culture were taken and filtered through a 0.2 micron Acrodisc filter to remove cells. The filtrate from this step contains the nitrite or nitrate to be analyzed. The analysis was performed on a Dionex ion chromatograph 500 system (Dionex, Sunnyvale, Calif.) with an AS3500 autosampler. The column used was a 4 mm Ion-Pac AS11-HC separation column with an AG-AC guard column and an ATC trap column. All columns are provided by Dionex.

The mobile phase was a potassium hydroxide gradient from 0 to 50 mM potassium hydroxide over a 12 min time interval. Cell temperature was 35° C. with a flow rate of 1 mL/min.

Microarray of Gene Expression

Amplification of DNA Regions for the Construction of DNA Microarray: Specific primer pairs were used to amplify each protein specifying ORF of *Methylomonas* sp. strain 16a. Genomic DNA (10–30 ng) was used as the template. The PCR reactions were performed in the presence of HotStart Taq™ DNA polymerase (Qiagen, Valencia, Calif.) and the dNTPs (Gibco BRL Life Science Technologies, Gaithersburg, Md.). Thirty-five cycles of denaturation at 95° C. for 30 sec, annealing at 55° C. for 30 sec and polymerization at 72° C. for 2 min were conducted. The quality of PCR reactions was checked with electrophresis in a 1% argarose gel. The DNA samples were purified by the high-throughput PCR purification kit from Qiagen.

Arraying Amplified ORFs. Before arraying, an equal volume of DMSO (10 µL) and DNA (10 µL) sample was mixed in 384-well microtiter plates. A generation II DNA spotter (Molecular Dynamics, Sunnyvale, Calif.) was used to array the samples onto coated glass slides (Telechem, Sunnyvale, Calif.). Each PCR product was arrayed in duplicate on each slide. After cross-linking by UV light, the slides were stored under vacuum in a desiccator at room temperature.

RNA Isolation: *Methylomonas* 16a was cultured in a defined medium with ammonium or nitrate (10 mM) as nitrogen source under 25% methane in air. Samples of the minimal medium culture were harvested when the O.D. reaches 0.3 at A$_{600}$ (exponential phase). Cell cultures were harvested quickly and ruptured in RLT buffer [Qiagen RNeasy Mini Kit, Valencia, Calif.] with a beads-beater (Bio101, Vista, Calif.). Debris was pelleted by centrifugation for 3 min at 14,000×g at 4° C. RNA isolation was completed using the protocol supplied with this kit. After on-column DNAase treatment, the RNA product was eluted with 50–100 µL RNAase-free. RNA preparations were stored frozen at either −20 or −80° C.

Synthesis of Fluorescent cDNA from Total RNA. RNA samples (7 to 15 µg) and random hexamer primers (6 µg; Gibco BRL Life Science Technologies) were diluted with RNAase-free water to a volume of 25 µL. The sample was denatured at 70° C. for 10 min and then chilled on ice for 30 seconds. After adding 14 µL of labeling mixture, the annealing was accomplished by incubation at room temperature for 10 min. The labeling mixture contained 8 µL of 5× enzyme buffer, 4 µL DTT (0.1M), and 2 µL of 20× dye mixture. The dye mixture consisted of 2 mM of each dATP, dGTP, and dTTP, 1 mM dCTP, and 1 mM of Cy3-dCTP or Cy5-dCTP. After adding 1 to 1.5 µL of SuperScript II reverse transcriptase (200 units/mL, Life Technologies Inc., Gaithersburg, Md.), cDNA synthesis was allowed to proceed at 42° C. for 2 hr. The RNA was removed by adding 2 µL NaOH (2.5 N) to the reaction. After 10 min of incubation at 37° C., the pH was adjusted with 10 µL of HEPES (2M). The labeled cDNA was then purified with a PCR purification kit (Qiagen, Valencia, Calif.). Labeling efficiency was monitored using either A$_{550}$ for Cy3 incorporation, or A$_{650}$ for Cy5.

Fluorescent Labeling of Genomic DNA. Genomic DNA was nebulized to approximately 2 kb pair fragments. Genomic DNA (0.5 to 1 µg) was mixed with 6 µg of random hexamers primers (Gibco BRL Life Science Technologies) in 15 µL of water. The mix was denatured by put at boiling water for 5 minutes. Then anneal on ice for 30 sec before put at room temperature. Then 2 µL 5× Buffer 2 (Gibco BRL) and 2 ul dye mixture were added. The component of dye mixture and the labeling procedure are the same as described above for RNA labeling, except that the Klenow fragment of DNA polymerase I (5 µg/µL, Gibco BRL Life Science Technologies) was used as the enzyme. After incubation 37° C. for 2 hr, the labeled DNA probe was purified using a PCR purification kit (Qiagen, Valencia, Calif.).

Hybridization and Washing. Slides were first incubated with prehybridization solution containing 3.5×SSC (BRL, Life Technologies Inc., Gaithersburg, Md.), 0.1% SDS (BRL, Life Technologies Inc., Gaithersburg, Md.), 1% bovine serum albumin (BSA, Fraction V, Sigma, St. Louis, Mo.). After prehybridization, hybridization solutions (Molecular Dynamics) containing labeled probes was added to slides and covered with cover slips. Slides were placed in a humidified chamber in a 42° C. incubator. After overnight hybridization, slides were initially washed for 5 min at room temperature with a washing solution containing 1×SSC, 0.1% SDS and 0.1×SSC, 0.1% SDS. Slides were then washed at 65° C. for 10 min with the same solution for three times. After washing, the slides were dried with a stream of nitrogen gas.

Data Collection and Analysis. The signal generated from each slide was quantified with a laser scanner (Molecular Dynamics, Sunnyvale, Calif.). The images were analyzed with ArrayVision 4.0 software (Imaging Research, Inc., Ontario, Canada). The raw fluorescent intensity for each spot was adjusted by subtracting the background. These readings were exported to a spreadsheet for further analysis.

Example 1

Isolation of *Methylomonas* 16a

The original environmental sample containing the isolate was obtained from pond sediment. The pond sediment was inoculated directly into defined medium with ammonium as nitrogen source under 25% methane in air. Methane was the sole source of carbon and energy. Growth was followed until the optical density at 660 nm was stable whereupon the culture was transferred to fresh medium such that a 1:100 dilution was achieved. After 3 successive transfers with methane as sole carbon and energy source the culture was plated onto growth agar with ammonium as nitrogen source and incubated under 25% methane in air. Many methanotrophic bacterial species were isolated in this manner.

However, *Methylomonas* 16a was selected as the organism to study due to the rapid growth of colonies, large colony size, ability to grow on minimal media, and pink pigmentation indicative of an active biosynthetic pathway for carotenoids.

Example 2

Rapid Growth on Methane in Minimal Medium

Figure 5:
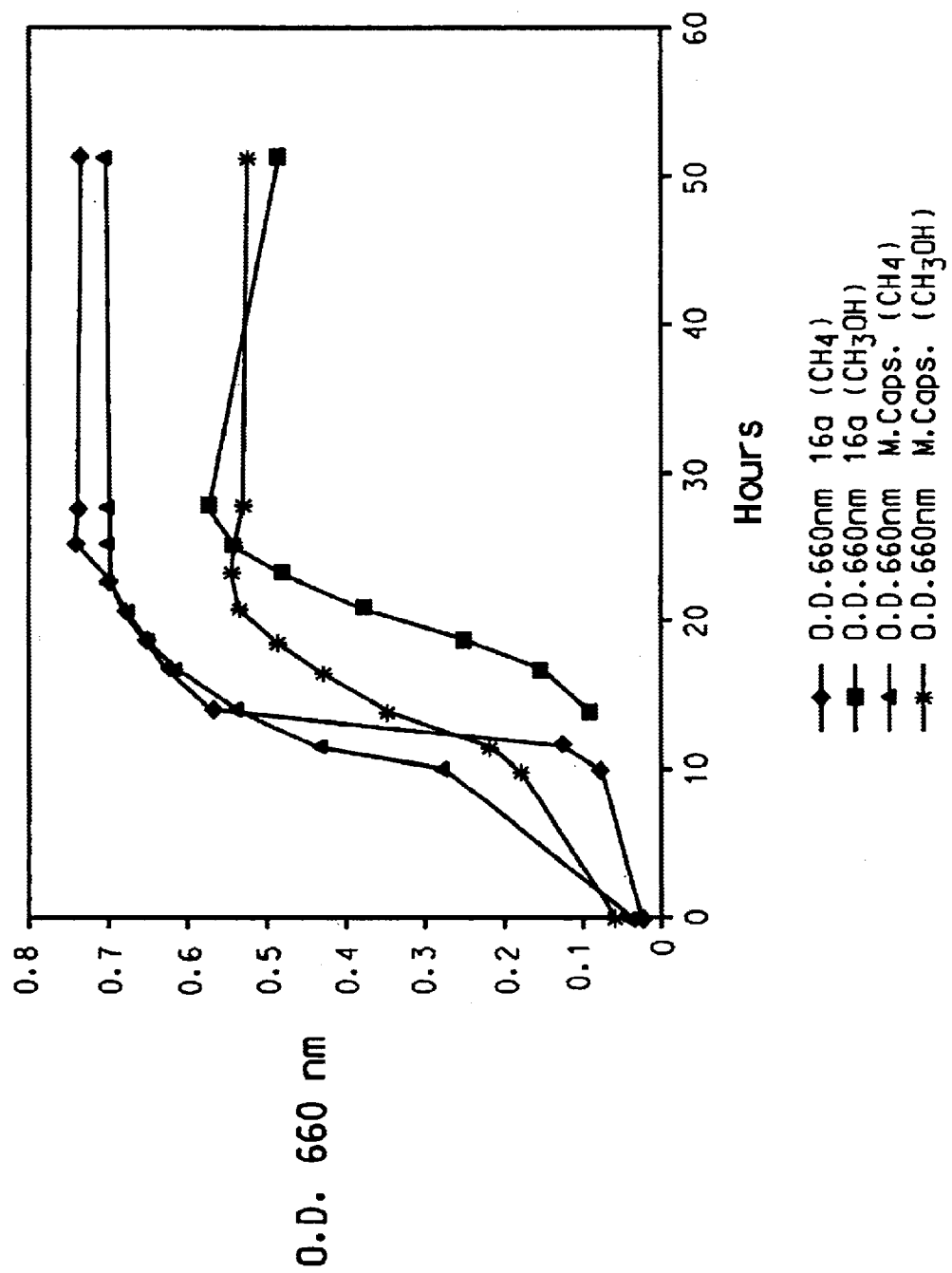
FIG. 5 shows the growth of *Methylomonas* 16a compared to the growth of *Methylococcus capsulatus* under identical growth conditions.

*Methylomonas* 16a grows on the defined medium comprised of only minimal salts, a culture headspace comprised of methane in air. Methane concentrations for growth but typically are 5–50% by volume of the culture headspace. No organic additions such as yeast extract or vitamins are required to achieve growth shown in FIG. 5. FIG. 5 shows the growth of 16a compared to the growth of *Methylococcus capsulatus* under identical growth conditions. i.e. minimal medium with 25% methane in air as substrate. The data indicates *Methylomonas* 16a doubles every 2–2.5 h whereas *Methylococcus capsulatus* doubles every 3.5 h with methane as substrate. With methanol as substrate doubling times on methanol are 2.5–3 for *Methylomonas* 16a and 4.5–5 for *Methylococcus capsulatus*. Cell densities are also significantly higher for *Methylomonas* 16a growing on methane. *Methylococcus capsulatus* is a widely utilized methanotroph for experimental and commercial purposes.

Example 3

Comparison of Gene Expression Levels in the Entner Douderoff Pathway as Compared with the Embeden Meyerof Pathway Example 3 presents microarray evidence for the use of the Embden-Meyerhoff pathway in the 16a strain.

Figure 6:
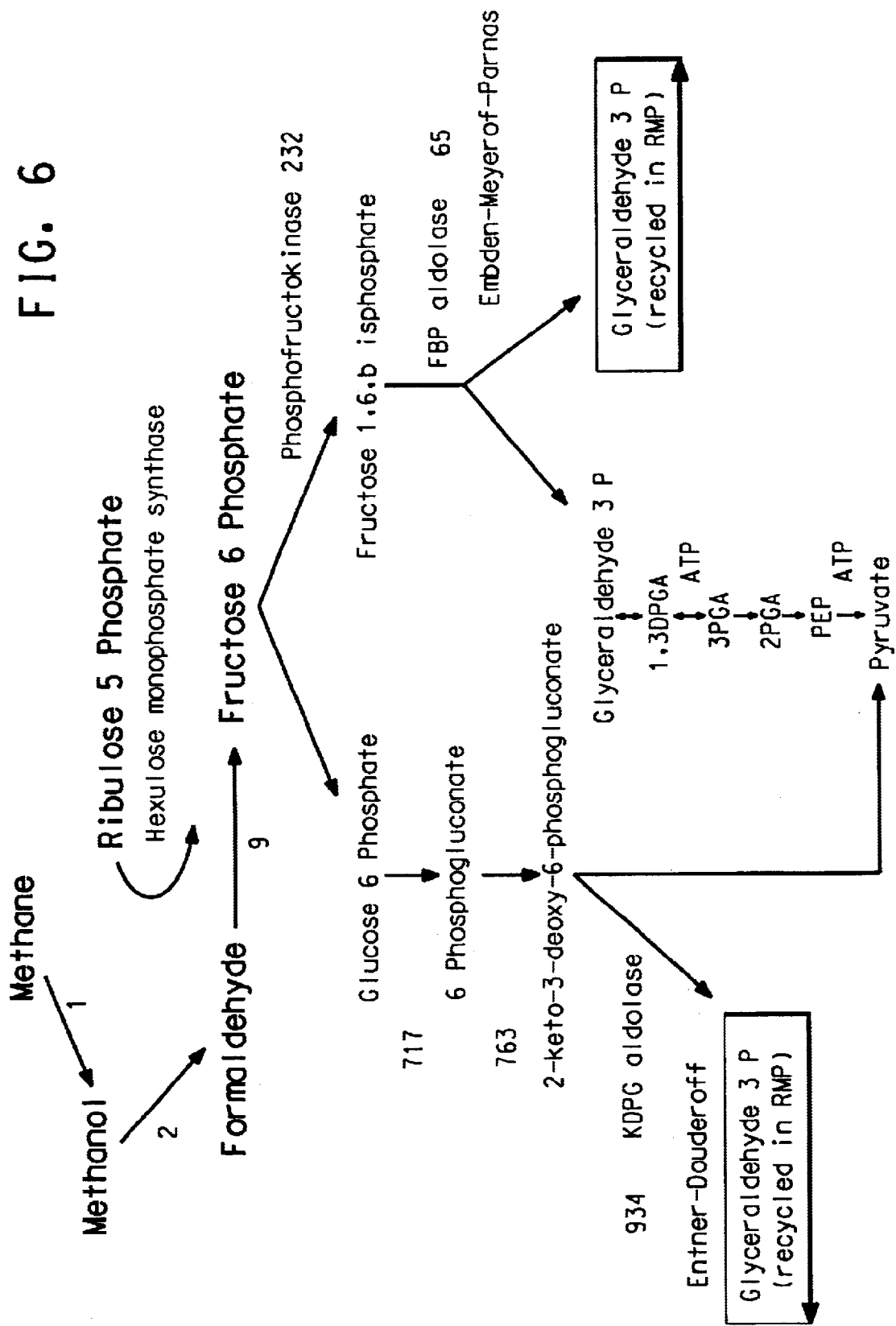
FIG. 6 is a Schematic of Entner-Douderoff and Embden-Meyerhoff pathways in *Methylomonas* 16a showing microarray expression results numerically ranked in order of decreasing expression level.

FIG. 6 shows the relative levels of expression of genes for the Entner-Douderoff pathway and the Embden-Meyerhof pathway. The relative transcriptional activity of each gene was estimated with DNA microarray as described previously (Wei, et al., 2001. *Journal of Bacteriology*. 183:545–556).

Specifically, a single DNA microarray containing 4000 ORFs (open reading frames) of *Methylomonas* sp. strain 16a was hybridized with probes generated from genomic DNA and total RNA. The genomic DNA of 16a was labeled with Klenow fragment of DNA polymerase and fluorescent dye Cy-5, while the total RNA was labeled with reverse transcriptase and Cy-3. After hybridization, the signal intensities of both Cy-3 and Cy-5 for each spot in the array were quantified. The intensity ratio of Cy-3 and Cy-5 was then used to calculate the fraction of each transcript (in percentage) with the following formula: (gene ratio/sum of all ratio)×100. The value obtained reflects the relative abundance of mRNA of an individual gene. Accordingly, transcriptional activity of all the genes represented by the array can be ranked based on its relative mRNA abundance in a descending order. For example, mRNA abundance for the methane monooxygenase was ranked #1 because its genes had the highest transcriptional activity when the organism was grown with methane as the carbon source (FIG. 6).

The genes considered "diagnostic" for Entner-Douderoff are the 6 phosphogluconate dehydratase and the 2 keto-3-deoxy-6-phosphogluconate aldolase. Phosphofructokinase and fructose bisphosphate aldolase are "diagnostic" of the Embden-Meyerhof sequence. Numbers in FIG. 6 next to each step indicate the relative expression level of that enzyme. For example the most highly expressed enzyme in the cell is the methane monooxygenase (ranked #1). The next most highly expressed is the methanol dehydrogenase (ranked #2). Messenger RNA transcripts of Phosphofructokinase (ranked #232) and fructose bisphosphate aldolase (ranked #65) were in higher abundance than those for glucose 6 phosphate dehydrogenase (ranked #717), 6 phosphogluconate dehydratase (ranked #763) or the 2-keto-3-deoxy-6-gluconate aldolase. The data suggests that the Embden-Meyerhof pathway enzymes are more strongly expressed than the Entner-Douderoff pathway enzymes. This result is surprising and counter to existing beliefs on the central metabolism of methanotrophic bacteria (Reference book pages in. The physiology and biochemistry of aerobic methanol-utilizing gram-negative and gram-positive bacteria In: Methane and Methanol Utilizers, Biotechnology Handbooks 5. 1992. Eds: Colin Murrell, Howard Dalton. Pp. 149–157.

Example 4

Direct Enzymatic Evidence for a Pyrophosphate-Linked Phosphofructokinase

Example 4 shows the evidence for the presence of a pyrophosphate-linked phosphofructokinase enzyme in the current strain which would confirm the functionality of the Embden-Meyerhof pathway in the present strain.

Phosphofructokinase activity was shown to be present in *Methylomonas* 16a by using the coupled enzyme assay described below. Assay conditions are given in Table 2 below. This assay was further used to assay the activity in a number of other Methanotrophic bacteria as shown below in Table 3. The data in Table 3 how known ATCC strains tested for phosphofructokinase activity with ATP or pyrophosphate as phosphoryl donor. These organisms were classified as either Type I or Type X ribulose monophosphate-utilizing strains or Type II serine utilizer.

Coupled Assay Reactions

Phosphofructokinase reaction was measured by a coupled enzyme assay. Phosphofructokinase reaction was coupled with fructose 1,6, biphosphate aldolase followed by triosephosphate isomerase. The enzyme activity was measured by the disappearance of NADH.

Specifically, the enzyme phosphofructokinase catalyzes the key reaction converting Fructose 6 phosphate and pyrophosphate to Fructose 1,6 bisphosphate and orthophosphate. Fructose-1,6-bisphosphate is cleaved to 3-phosphoglyceraldehyde and dihydroxyacetonephosphate by fructose 1,6-bisphosphate aldolase. Dihydroxyacetonephosphate is isomerized to 3-phosphoglyceraldehyde by triosephosphate isomerase. Glycerol phosphate dehydrogenase plus NADH and 3-phosphoglyceraldehyde yields the alcohol glycerol-3-phosphate and NAD. Disappearance of NADH is monitored at 340 nm using spectrophotometer (UltraSpec 4000, Pharmacia Biotech).

TABLE 2

Assay Protocol

| Reagent | Stock solution (mM) | Volume (µl) per 1 mL total reaction volume | Final assay concentration (mM) |
| --- | --- | --- | --- |
| Tris-HCl pH 7.5 | 1000 | 100 | 100 |
| $MgCl_2.2H_2O$ | 100 | 35 | 3.5 |
| $Na_4P_2O_7.10H_2O$ | 100 | 20 | 2 |

TABLE 2-continued

Assay Protocol

| Reagent | Stock solution (mM) | Volume (µl) per 1 mL total reaction volume | Final assay concentration (mM) |
|---|---|---|---|
| or ATP | | | |
| Fructose-6-phophate | 100 | 20 | 2 |
| NADH | 50 | 6 | 0.3 |
| Fructose bisphosphate aldolase | 100 (units/mL) | 20 | 2 (units) |
| Triose phosphate isomerase/glycero 1 phosphate dehydrogenase | (7.2 units/µl) (0.5 units/µl) | 3.69 | 27 units 1.8 units |
| KCl | 1000 | 50 | 50 |
| H2O | | adjust to 1 mL | |
| Crude extract | | 0–50 | |

TABLE 3

Comparison Of Pyrophosphate Linked And ATP Linked Phosphofructokinase Activity In Different Methanotrophic Bacteria

| Strain | Type | Assimilation Pathway | ATP-PFK umol NADH/ min/mg | Ppi-PFK umol NADH/ min/mg |
|---|---|---|---|---|
| Methylomonas 16a ATCC PTA 2402 | I | Ribulose monophosphate | 0 | 2.8 |
| Methylomonas agile ATCC 35068 | I | Ribulose monophosphate | 0.01 | 3.5 |
| Methylobacter Whittenbury ATCC 51738 | I | Ribulose monophosphate | 0.01 | 0.025 |
| Methylomonas clara ATCC 31226 | I | Ribulose monophosphate | 0 | 0.3 |
| Methylomicrobium albus ATCC 33003 | I | Ribulose monophosphate | 0.02 | 3.6 |
| Methylococcus capsulatus ATCC 19069 | X | Ribulose monophosphate | 0.01 | 0.04 |
| Methylosinus sporium ATCC 35069 | II | Serine | 0.07 | 0.4 |

Several conclusions may be drawn from the data presented above. First, it is clear that ATP (which is the typical phosphoryl donor for phosphofructokinase) is essentially ineffective in the phosphofructokinase reaction in methanotrophic bacteria. Only inorganic pyrophosphate was found to support the reaction in all methanotrophs tested. Secondly not all methanotrophs contain this activity. The activity was essentially absent in *Methylobacter whittenbury* and in *Methylococcus capsulatus*. Intermediate levels of activity were found in *Methylomonas clara* and *Methylosinus sporium*. These data show that many methanotrophic bacteria may contain a hitherto unreported phosphofructokinase activity. It may be inferred from this that methanotrophs containing this activity have an active Embden-Meyerhof pathway.

Example 5

Growth Yield and Carbon Conversion by *Methylomonas* 16a

Growth yield and carbon conversion efficiency were compared for *Methylomonas* 16a and *Methylococcus capsulatus*. These strains were chosen because 16a contains high levels of phosphofructokinase and *M. capsulatus* is essentially devoid of the enzyme activity. It was contemplated that if *Methylomonas* 16a could utilize the more energetically favorable Embden-Meyerhof pathway and *Methylococcus capsulatus* could only use the Entner-Douderoff pathway the superior energetics of the present *Methylomonas* 16a strain would be reflected in cellular yields and carbon conversion efficiency. This difference in energetic efficiency would only be apparent under energy-limiting conditions. These conditions were achieved in this experiment by limiting the amount of oxygen in each culture to only 10% (vol/vol) instead of 20%. Under these oxygen limiting conditions the strain that produces the most energy from aerobic respiration on methane will produce more cell mass.

Cells were grown as 200 mL cultures 500 mL serum-stoppered Wheaton bottles. The headspace in the bottles was adjusted to 25% methane and 10% oxygen. The defined medium formulation is the same in both cases.

TABLE 4

Yield Of Methylomonas 16a Cells Versus Methylococcus Capsulatus Cells Under Oxygen Limitation.

| Strain | $Y_{CH4\ g\ dry\ wt/mol}$ | G dry wt/g $CH_4$ | Carbon Conversion Efficiency (CCE)% |
|---|---|---|---|
| Methylomonas 16a | 16.7 +/− 0.5 | 1.04 | 64 |
| Methylococcus capsulatus | 10.3 +/− 0.3 | 0.64 | 40 |

Yield Determination: Yield was measured by growing triplicate cultures in 500 mL bottles on defined medium with ammonium as nitrogen source under oxygen limitation. This was done by using 300 mL of culture with a 300 mL headspace of 25% methane and 10% oxygen the balance being nitrogen. At the end of growth (i.e. stationary phase) residual methane in the headspace was determined by gas chromatography. The cells were collected by centrifugation washed with distilled water and dried overnight in a drying oven before being weighed.

Carbon conversion efficiency is a measure of how much carbon is assimilated into cell mass. It is calculated assuming a biomass composition of $CH_2O_{0.5}N_{0.25}$:

Methylomonas 16a:16 g/mol methane×(1 g dry wt/g methane)/25 g/mol biomass

M. capsulatus 16 g/mol methane×(0.64 g dry wt/g methane)/25 g/mol biomass

These data (in Table 4) show that Methylomonas 16a produced significantly more cell mass than did the Methylococcus capsulatus strain under growth conditions that were identical except for the temperature. Methylococcus capsulatus grows optimally at 45° C. whereas Methylomonas is grown at 33° C. It may be inferred from the data that the presence of the more energy-yielding Embden-Meyerhof pathway confers a growth advantage to Methylomonas 16a.

Table 5 presents the theoretical calculations showing ATP yield as a function of carbon assimilation pathway with the carbon output being normalized to pyruvate in all cases (The physiology and biochemistry of aerobic methanol-utilizing gram-negative and gram-positive bacteria In: Methane and Methanol Utilizers, Biotechnology Handbooks 5. 1992. Eds: Colin Murrell, Howard Dalton. Pp. 149–157). Table 5 shows the amount of ATP that is produced or consumed for every three molecules of carbon (as formaldehyde or carbon dioxide) for serine cycle, xylulose monophosphate cycle and ribulose monophosphate cycle pathways. The latter pathway, as discussed is typically thought to exist as the 2-keto-3deoxy-6-phosphogluconate/transaldolase (KDPGA/TA) variant. These data shows that in fact the fructose bisphosphate aldolase/transaldolase (FBPA/TA) variant is likely to exist in the methanotrophs. The energetic repercussion of this is the net production of an additional 1 ATP for methanotrophs if they possess an ATP linked phosphofructokinase and an additional 2 ATPs for the pyrophosphate-linked enzyme. It is therefore expected that Methylomonas 16a derives and additional 2 ATP per 3 carbons assimilated and that this may explain the greater yield and carbon efficiency of the strain versus Methylococcus capsulatus.

electrophoresis and QIAEX II Gel Extraction (Qiagen Cat.# 20021). The 4 base pair 5' overhang (5'-TATG-3') gap was filled using T4 DNA polymerase (Gibco BRL Cat.# 18005-017), maintaining the methionene start codon immediately preceding the arginine codon which corresponds to amino acid number 58 in the native gene. Concurrently, the 3' BamH1 overhang was filled in by the same enzyme without interuption of the native limonene synthase stop codon. The blunt ended insert was purified using the QIAquick PCR Purification Kit (Qiagen Cat# 28104).

The vector pTJS75:dxS:dxR:Tn5Kn is a derivative of RK2, a broad-host-range plasmid (J. Bact., 164, 446–455) modified to include kanamycin resistance and two Methylomonas genes of interest: dxs, encoding 5'deoxy-D-xylulose synthase and dxr, encoding 5'deoxy-D-xylulose reductoisomerase. This vector was prepared for ligation by digesting with XhoI, blunting the overhangs with T4 DNA Polymerase, dephosphorylating with Calf Intestinal Alkaline Phosphatase (GibcoBRL), and purifying on a QIAquick PCR Purification column.

Figure 1:
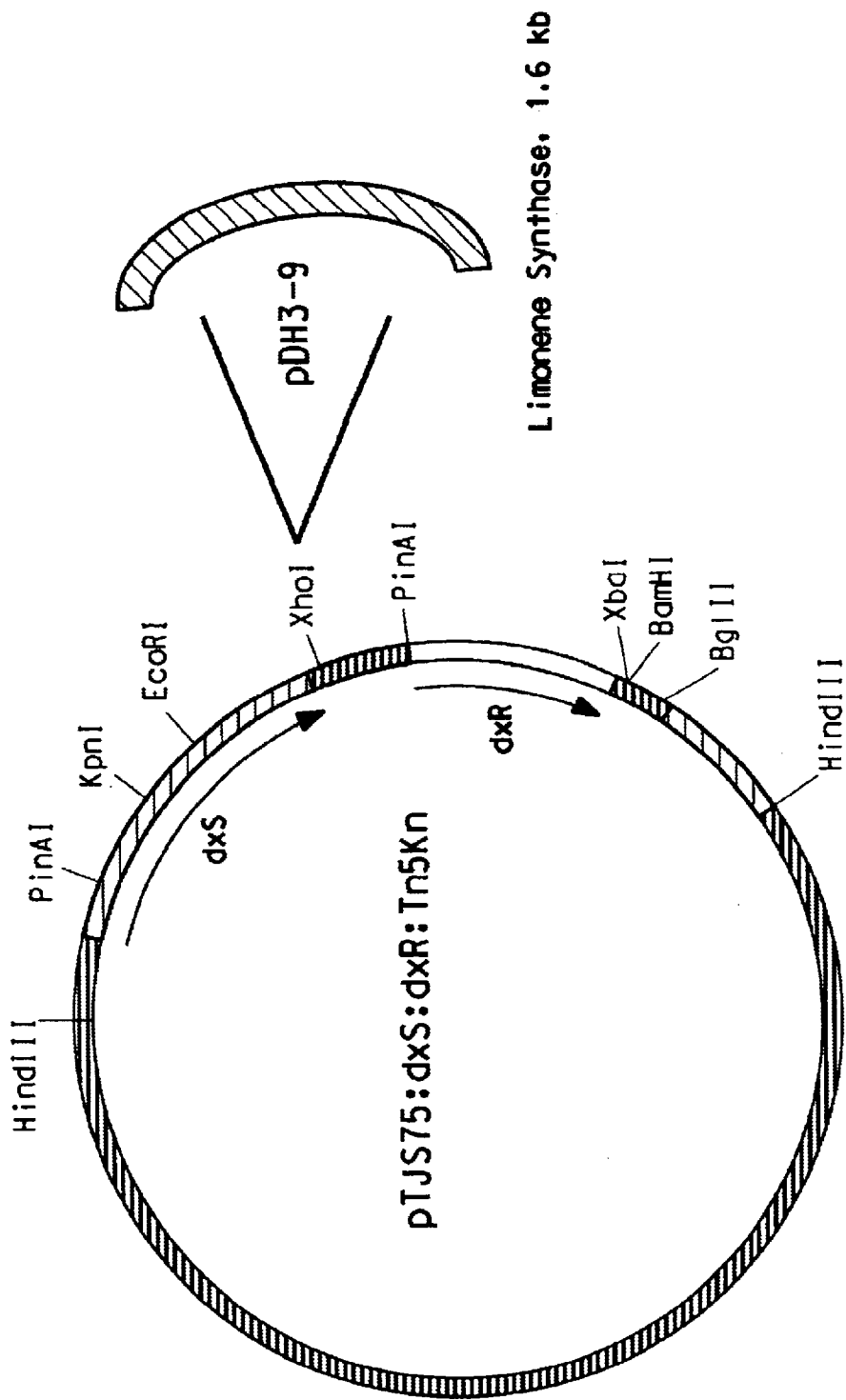
FIG. 1 shows the map of pTJS75:dxs:dxr:Tn5Kn plasmid containing truncated limonene synthase gene.

The limonene synthase gene insert was ligated into the vector and electroporated into E. coli electroMAX DH10B cells (Gibco BRL). The resulting plasmid, designated pDH3, contains the limonene synthase gene flanked on the 5'end by dxS and on the 3'end by dxR (FIG. 1).

Plasmid pDH3 was transferred into Methylomonas sp. 16a by triparental conjugal mating. Fresh overnight cultures of E. coli helper pRK2013 and E. coli donor DH10B/pDH3 along with vector (pTJS75:dxS:dxR:Tn5Kn) control grown in LB (Luria-Bertani medium) with kanamycin (50 μg/mL) were washed three times in plain LB, and resuspended in a volume of LB representing approximately a 60-fold concentration of the original culture volume. Recipient cells, a rifampicin resistant subculture of Methylomonas sp. 16a (designated 16aA), were grown for 48 hours in BTZ-3 (Table 1) with rifampicin (50μg/mL) under 25% methane, washed three times in BTZ-3, and resuspended in a volume of BTZ-3 representing approximately a 150-fold concentration of the original culture volume. The resulting donor, helper, and recipient cell pastes were combined on the surface of BTZ-3 agar plates containing 0.5% (w/v) yeast extract in ratios of 1:1:2 respectively. Plates were maintained at 25% methane for 16–24 hours to allow conjugation to

TABLE 5

Energetics of Methanotrophic bacteria utilizing different carbon assimilation mechanisms

| Organism | Cycle | C1 unit fixed | Product | Variant | ATP | NADPH |
| --- | --- | --- | --- | --- | --- | --- |
| Bacteria | RuMP | 3CH$_2$O | Pyruvate | FBPA/TA | +1 | +1 |
| Methylomonas | RuMP/Serine | 3CH$_2$O | Pyruvate | FBPA/TA | +1(+2*) | +1 |
| Bacteria | RuMP | 3CH$_2$O | Pyruvate | KDPGA/TA | 0 | +1 |
| Methylococcus | RuMP/RuBP | 3CH$_2$O | Pyruvate | KDPGA/TA | 0 | +1 |

*Based on PPi dependent phosphofructokinase

Example 6

Plasmid Construction

The plasmid pR58 contains Mentha spicata limonene synthase gene which carries a deletion of the first 57 amino acids of the enzyme (Williams et al, Biochemistry 1998, 37, 12213–12220). pR58 was digested with restriction enzymes NdeI and BamH1, releasing the truncated limonene synthase. The 1638 base pair gene was purified by agarose gel occur. Cell pastes were harvested and resuspended in BTZ-3. Serial dilutions were plated on BTZ-3 agar with rifampicin (50 μg/mL) and kanamycin (50 μg/mL). Resulting colonies were patched to new selective plates. Colonies which grew the second time were then transferred to liquid BTZ-3 with rifampicin (50 μg/mL) and kanamycin (50 μg/mL). The presence of the limonene synthase gene in the 16a conjugates was verified by PCR using primer set 5'-atgagacgatccggaaactacaaccc-3' (SEQ ID NO:1) and 5'-tcatgcaaagggctcgaataaggttctgg-3' (SEQID NO:2) which anneals to the N- and C-terminus of the limonene synthase respectively. The primer set 5'-atgattgaacaagatggattgc-3' (SEQID NO:3) and 5'-aagctttcaaaagaactcgtc-3' (SEQID NO:4) was used to detect kanamycin resistance gene as a control.

Example 7

Limonene Detection

Liquid cultures of *Methylomonas* sp. 16a transconjugants were grown in airtight bottles for approximately 48 hours in BTZ-3 supplemented with rifampicin (50 µg/mL), kanamycin (50 µg/mL) and 25% methane. Contents of the culture vessel were harvested for limonene and analyzed by gas chromatography (GC) analysis. Briefly, ethyl acetate was injected through the septa in order to extract limonene from both the headspace and from the liquid. Samples were agitated for 5 min., transferred to appropriate centrifuge tubes and centrifuged to achieve complete separation of the organic and aqueous phases. The organic phase was removed and loaded onto a DB-1 column (30M/0.25 ID/0.25 film thickness, J&W Scientific, Folsom, Calif.).

The initial oven temperature was set at 50° C. and temperature was increased to 250° C. at a rate of 10 degrees per minute. After 5 minutes at 250° C., the samples were injected into the column. A Septum purge was applied for one minute at a rate of 2.4 mL per minute. The runs were carried out at a head pressure of 8 psi and flow rate of 24.5 mL per minute. Limonene used as a standard was purchased from Sigma-Aldrich (Cat#18,316-4). Samples analyzed by GC/MS are identical to those analyzed by GC alone. GC/MS instrument type: ProSpec. Source type: Combined-EI/CI SRC. Electron energy: 69.0 eV. Multiplier voltages: #1: 198.6 V, #2: 250.0 V, #3: 250.0 V, #4: 250.0 V. Emission current: 0.0 mA Trap current: 444.1 µA. Ion repeller: 5.7 V. Source temp: 225.3° C. Extraction heater current: 0.0 mA. Slit criteria: Source: 47.8%, Collector: 50.4%, Alpha: 100%, Z2 Restrict: 0.0%, Z3 Restrict: 0.0%, Z4 Restrict: 0.0%. Lens Criteria: Ion Energy: 1.4, Focus#1: 2.2 V, Beam Centre: −48.7 V, Focus #2: 5.8 V, Y-Focus: 4.4 V, Y-Def#1: −88.0 V, Z-Def#1: 7.5 V, Rotate #1: 0.0 V, Z-Def#2:−12.6 V, Z-Focus #2: 6.0V, Rotate #2: −13.6 V, Curve #2: −4.0 V, Curve #3: −8.6 V, Rotate #3: −9.0 V, Z-Focus #3: 9.3 V, Z-Def#3: 0.0 V, Rotate #4: 0.0 V. Magnet parameters: IMR 1160.16, Standard coil. No ramped parameters. HP6890 GC parameters: Automatic restart, Capillary line temp (1): 240.0° C., Capillary line temp (2): 240.0° C., Reentrant temp: 240.0° C., Maximum oven temp: 325.2° C., Equilibrium time: 0.2 min, Oven Temperature Ramps: Temp #1: 50.0° C., Time #1: 1.0 min, Rate #1: 10.0° C./min, Temp#2: 200.0° C., Time #2: 1.0 min, Rate #2: 10.0° C./min, Temp #3: 250.0° C., Time #3: 10.0 min, Rate #3: 0.0° C./min. Injectors: "A": Active, Injector "A" temp: 270.0° C., Injection type: splitless, Purge "A" on time: 1.0 min, Purge "A" Flow: 1.0 mL/min, Col 1 Const Flow: 1.0 mL/min. "B": Active, Injection type: Cool-on-Col, "B" Injector Temp Ramps: Temp #1: 50.0° C., Time #1: 650.0 min, Rate #1: 0.0° C./min, Col 1 Const flow: 2.0 mL/min.

Figure 2:
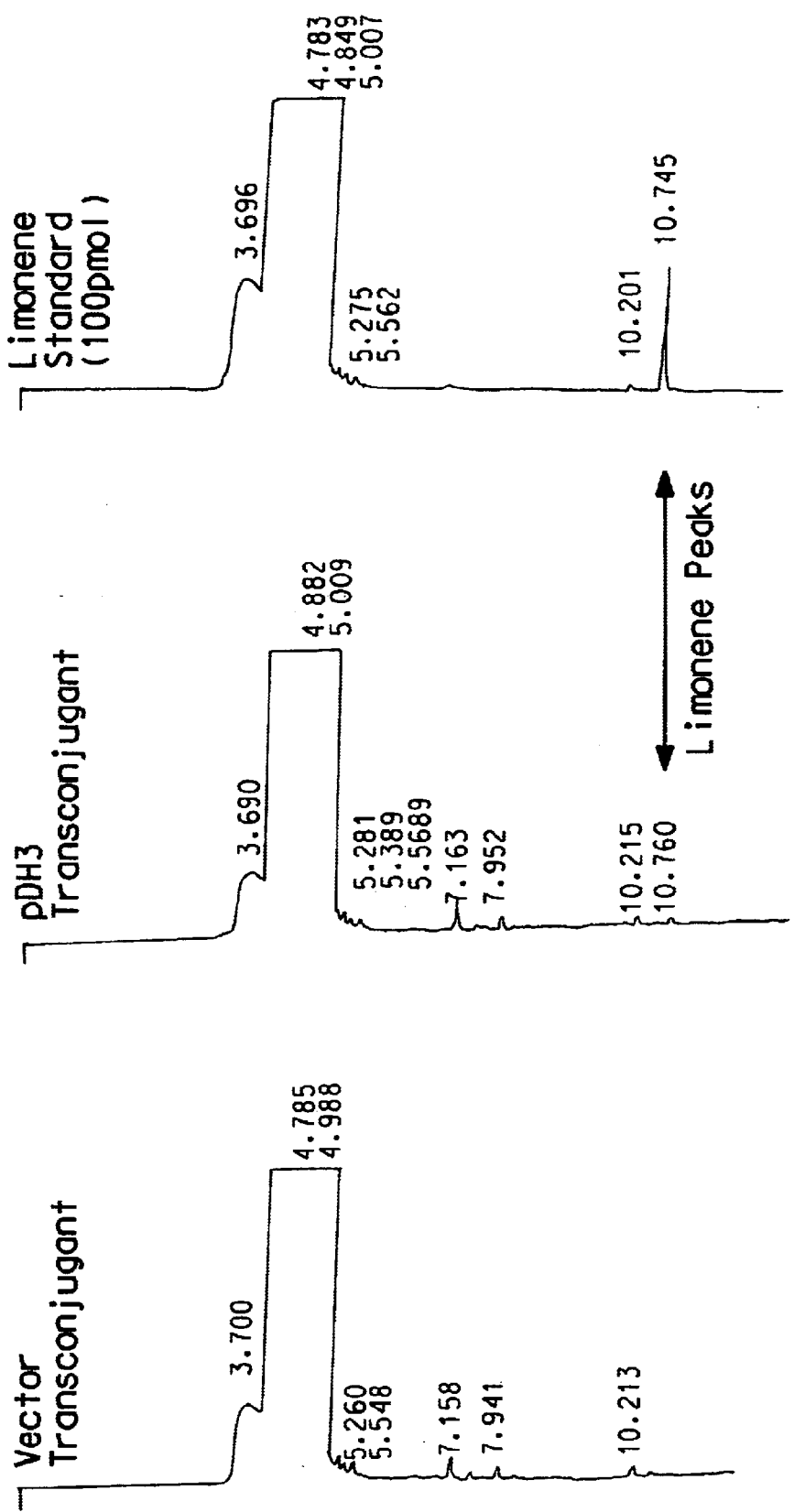
FIG. 2 shows the gas chromatography analysis of limonene produced in *Methylomonas* 16a culture.

*Methylomonas* sp. 16a which received the limonene synthase gene produced limonene (~0.5 ppm). In the GC analysis, chromatograms of these extracts display a peak which is superimposable with that of the limonene standard (FIG. 2). As expected, *Methylomonas* sp. 16a alone or *Methylomonas* sp. 16a containing vector pTJS75:dxS:dxR:Tn5Kn did not produce any detectable limonene. The presence or absence of limonene was further confirmed by GC/MS. The limonene peak from GC generated identical fragmentation patterns as the limonene standard with a signature peak at 68 and predicted MW at 136. The level of production was comparable in the two assays.

What is claimed is:

1. A method for the production of a monoterpene comprising:
   a) providing a transformed *Methylomonas* cell comprising:
      (i) geranyl pyrophosphate; and
      (ii) at least one isolated nucleic acid molecule encoding a cyclic terpene synthase selected from the group consisting of limonene synthase, inene synthase, bornyl synthase, phellandrene synthase, cineole synthase and sabinene synthase under the control of suitable regulatory sequences;
   b) contacting the *Methylomonas* cell of step (a) under suitable growth conditions with an effective amount of a C1 carbon substrate whereby a monoterpene compound is produced.

2. A method according to claim 1 wherein the C1 carbon substrate is methane.

3. A method according to claim 1 wherein the *Methylomonas* is a high growth methanotrophic strain which comprises a functional Embden-Meyerof carbon pathway, said pathway comprising a gene encoding a pyrophosphate dependent phosphofructokinase enzyme.

4. A method according to claim 3, wherein the high growth methanotrophic bacterial strain optionally contains a functional Entner-Douderoff carbon pathway.

5. A method according to claim 3, wherein the high growth methanotrophic bacterial strain is *Methylomonas* 16a having the ATCC designation ATCC PTA 2402.

6. A method according to claim 1 wherein the monoterpene is selected from the group consisting of limonene, pinene, barnyl diphosphate, β-phellandrene, 1,8-cineole, and sabinene.

7. A method according to claim 1 wherein the limonene synthase has the amino sequence as set forth in SEQ ID NO: 6.

* * * * *